(12) United States Patent
Aissaoui et al.

(10) Patent No.: US 8,889,688 B2
(45) Date of Patent: Nov. 18, 2014

(54) PIPERAZINES AS ANTIMALARIAL AGENTS

(75) Inventors: Hamed Aissaoui, Allschwil (CH);
Christoph Boss, Allschwil (CH);
Olivier Corminboeuf, Allschwil (CH);
Bibia Heidmann, Allschwil (CH);
Romain Siegrist, Allschwil (CH)

(73) Assignee: Actelion Pharmaceuticals Ltd.,
Allschwil (CH)

( * ) Notice: Subject to any disclaimer, the term of this patent is extended or adjusted under 35 U.S.C. 154(b) by 0 days.

(21) Appl. No.: 13/519,938

(22) PCT Filed: Jan. 4, 2011

(86) PCT No.: PCT/IB2011/050009
§ 371 (c)(1),
(2), (4) Date: Jun. 29, 2012

(87) PCT Pub. No.: WO2011/083413
PCT Pub. Date: Jul. 14, 2011

(65) Prior Publication Data
US 2012/0316178 A1 Dec. 13, 2012

(51) Int. Cl.
*A61K 31/497* (2006.01)
*C07D 403/12* (2006.01)
*A61K 31/496* (2006.01)

(52) U.S. Cl.
CPC ............ *A61K 31/496* (2013.01); *C07D 403/12* (2013.01)
USPC ...................................... 514/252.11; 544/357

(58) Field of Classification Search
USPC ...................................... 514/252.11; 544/357
See application file for complete search history.

(56) References Cited

U.S. PATENT DOCUMENTS 8,067,419 B2 11/2011 Binkert et al.

FOREIGN PATENT DOCUMENTS

| EP | 0 407 200 | 1/1991 |
|---|---|---|
| JP | 03 127732 | 5/1991 |
| WO | WO 00/15657 | 3/2000 |
| WO | WO 00/66566 | 11/2000 |
| WO | WO 02/098856 | 12/2002 |
| WO | WO 2004/032874 | 4/2004 |
| WO | WO 2005/013909 | 2/2005 |
| WO | WO 2005/058822 | 6/2005 |
| WO | WO 2007/046075 | 4/2007 |
| WO | WO 2009/141782 A1 | 11/2009 |
| WO | WO 2010/058353 A1 | 5/2010 |

OTHER PUBLICATIONS

Gould, P.L., "Salt Selection for Basic Drugs", International Journal of Pharmaceutics, 1986, vol. 33, 201-217.
Remington, The Science and Practice of Pharmacy, 21$^{st}$ Edition (2005), Part 5, "Pharmaceutical Manufacturing", [published by Lippincott Williams & Wilkins].
Written Opinion (Form PCT/ISA/237) for WO 2011/083413 issued Jul. 5, 2010.
Database Chemcats, Chemical Abstracts Service, Columbus, OH, USA; XP002420714; Order No. (ON): CGX-3221820 (Apr. 15, 2005).
Database Chemcats, Chemical Abstracts Service Columbus, OH, USA; XP002420715; Order No. (ON): T5569369, T5467386, (Jan. 24, 2006).
Gibson, Mark, Editor, Pharmaceutical Preformulation and Formulation, HIS Health Group, Englewood, CO, USA, (2001).
Gennaro, A.R., Editor, "Remington: The Science and Practice of Pharmacy", 20$^{th}$ Edition, Philadelphia College of Pharmacy and Science, Table of Contents, (2003).
Communication Pursuant to Article 94(3)EPC Application 06809659.3-2101, (Jul. 1, 2010).
Dorwald, F.A., "Side Reactions in Organic Synthesis", (2005), Wiley: VCH, Weinheim, p. IX of Preface.
Vippagunta et al., Advance Drug Delivery Reviews vol. 48, (2001), pp. 3-26.
Chawla, et al., Current Research and Information on Pharmaceutical Science, (2004), vol. 5, No. 1, p. 9, col. 2, para. 1.
Newman et al., Drug Discovery Today, (2003), vol. 8, No. 19, p. 898, col. 2, Para. 3.
Http://www.thefreedictionary.com/prevent, last accessed on Aug. 26, 2010.
Notice of Allowance of U.S. Appl. No. 12/090,816 dated Jul. 6, 2011.
Notice of Allowance of U.S. Appl. No. 12/090,816 dated Apr. 28, 2011.
Non-Final Rejection for U.S. Appl. No. 12/090,816 dated Sep. 1, 2010.
Restriction Requirement for U.S. Appl. No. 12/090,816 dated Jul. 15, 2010.
International Search Report for PCT/IB2006/053868 mailed Mar. 9, 2007.

*Primary Examiner* — Wu-Cheng Winston Shen
*Assistant Examiner* — Jean Cornet
(74) *Attorney, Agent, or Firm* — Hoxie & Associates LLC

(57) ABSTRACT

The invention relates to novel piperazine derivatives and their use as active ingredients in the preparation of pharmaceutical compositions. The invention also concerns related aspects including pharmaceutical compositions containing one or more of those compounds and their use as medicaments for the treatment or prevention of protozoal infections, such as especially malaria.

36 Claims, No Drawings

PIPERAZINES AS ANTIMALARIAL AGENTS

CROSS REFERENCE TO RELATED APPLICATIONS

This application is a United States National Stage Application under 35 U.S.C. 371 of PCT Application No. PCT/IB2011/050009, filed on Jan. 4, 2011, which claims the benefit of PCT Application No. PCT/IB2010/052045, filed May 10, 2010 and PCT Application No. PCT/IB2010/050022, filed on Jan. 5, 2010.

The invention relates to novel compounds of the formula I. The invention also concerns related aspects including processes for the preparation of the compounds, pharmaceutical compositions containing one or more compounds of the formula I and especially their use as medicaments to treat or prevent malaria infections or to treat or prevent other protozoal diseases like sleeping sickness, Chagas disease, amebiasis, giardiasis, trichomoniasis, toxoplasmosis, and leishmaniasis.

BACKGROUND OF THE INVENTION

Numerous serious diseases affecting humans as well as domestic and livestock animal are caused by protozoal organisms such as *kinetoplastida, apicomplexa, anaerobic protozoa, microsporidia* and *plasmodium*, for example. The clinically most relevant of these diseases is malaria.

Malaria is one of the most serious and complex health problems affecting humanity in the 21$^{st}$ century. The disease affects about 300 million people worldwide, killing 1 to 1.5 million people every year. Malaria is an infectious disease caused by four species of the protozoan parasite plasmodium, *P. falciparum* being the most severe of the four. All attempts to develop vaccines against *P. falciparum* have failed so far. Therefore, therapies and preventive measures against malaria are confined to drugs. Various classes of antimalarial drugs exist. The most widely used are the quinoline antimalarials, e.g. chloroquine which has been an especially effective drug for both prophylaxis and therapy. However, resistance to many of the currently available antimalarial drugs is spreading rapidly, threatening people in areas where malaria is endemic. Reports of multi-drug resistant strains of malaria parasites render the search for new antimalarial agents especially urgent. *P. falciparum* enters the human body by way of bites of the female anophelino mosquito (it may also be transmitted by blood transfusion from asymptotic donors; almost all infected blood components including red cells, platelet concentrates, white cells, cryoprecipitates and fresh plasma can transmit malaria). The plasmodium parasite initially populates the liver, and during later stages of the infectious cycle reproduces in red blood cells. During this stage, the parasite degrades hemoglobin and uses the degradation products as nutrients for growth.

The limitations of the current antiprotozoal chemotherapeutic arsenal underscore the need for new drugs in this therapeutic area. The present invention relates to the identification of novel low molecular weight, non-peptidic, non-quinoline compounds of formula I which are useful in the treatment and/or prevention of protozoal infections, especially in the treatment and/or prevention of malaria, in particular *plasmodium falciparum* malaria.

WO 2007/046075 also discloses piperazine derivatives as antimalarial agents. The compound of WO 2007/046075 which comes closest to some of the presently claimed compounds is the compound of Example 54 which corresponds to reference Example 1 herein. However, the presently claimed compounds which come structurally closest to the compound of Example 54 of WO 2007/046075 exhibit an in vitro activity against erythrocytic stages of the *P. falciparum* strain NF54 in the presence of 50% serum which is significantly higher compared to the compound of Example 54 of WO 2007/046075 (see Table 1 below).

DETAILED DESCRIPTION OF THE INVENTION i) The present invention relates to novel compounds of the formula I:

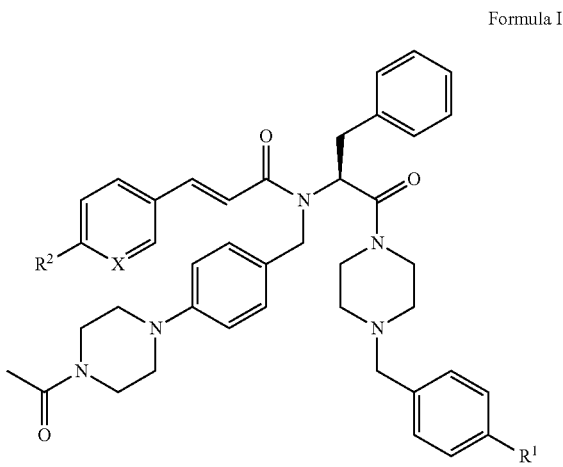

Formula I wherein
X is CH or N;
R$^1$ represents —NO$_2$, —N(CH$_3$)$_2$, or —NCH$_3$ (CH$_2$CH$_2$OH); and
R$^2$ represents hydrogen, methyl, ethyl, n-propyl, isopropyl, tert-butyl, cyano, halogen, methoxy, ethoxy, n-propoxy, isopropoxy, trifluoromethyl, difluoromethoxy, methylsulfonyl, acetyl, or acetylamino; or
X is CH, R$^1$ is hydrogen, and R$^2$ is ethyl, isopropyl, tert-butyl, ethoxy, n-propoxy, isopropoxy, methylsulfonyl, acetylamino, or methoxycarbonyl; or
X is CH, R$^1$ is cyano, and R$^2$ is ethyl, isopropyl, tert-butyl, ethoxy, n-propoxy, isopropoxy, trifluoromethyl, difluoromethoxy, trifluoromethoxy, methylsulfonyl, or acetylamino; or
X is CH, R$^1$ is chloro, and R$^2$ is ethyl, isopropyl, tert-butyl, ethoxy, n-propoxy, isopropoxy, difluoromethoxy, methylsulfonyl, or acetylamino; or
X is CH, R$^1$ is methoxy or isopropoxy, and R$^2$ is trifluoromethyl; or
X is CH, R$^1$ is methylsulfonyl or ethylsulfonyl, and R$^2$ is trifluoromethyl, ethyl, isopropyl, tert-butyl, ethoxy, n-propoxy, isopropoxy, or difluoromethoxy, such as especially trifluoromethyl, tert-butyl, n-propoxy, or isopropoxy.

ii) A further embodiment of the invention relates to compounds of the formula I according to embodiment i), wherein
X is CH or N;
R$^1$ represents —NO$_2$, —N(CH$_3$)$_2$, or —NCH$_3$ (CH$_2$CH$_2$OH); and
R$^2$ represents hydrogen, methyl, ethyl, n-propyl, isopropyl, tert-butyl, cyano, halogen, methoxy, ethoxy, n-propoxy, isopropoxy, trifluoromethyl, difluoromethoxy, methylsulfonyl, acetyl, or acetylamino; or X is CH, $R^1$ is hydrogen, and $R^2$ is ethyl, isopropyl, tert-butyl, ethoxy, n-propoxy, isopropoxy, methylsulfonyl, acetylamino, or methoxycarbonyl; or X is CH, $R^1$ is cyano, and $R^2$ is ethyl, isopropyl, tert-butyl, ethoxy, n-propoxy, isopropoxy, trifluoromethyl, difluoromethoxy, trifluoromethoxy, methylsulfonyl, or acetylamino; or X is CH, $R^1$ is chloro, and $R^2$ is ethyl, isopropyl, tert-butyl, ethoxy, n-propoxy, isopropoxy, difluoromethoxy, methylsulfonyl, or acetylamino; or X is CH, $R^1$ is methoxy or isopropoxy, and $R^2$ is trifluoromethyl.

iii) A further embodiment of the invention relates to compounds of the formula I according to embodiment i), wherein X is CH or N;

$R^1$ represents —$NO_2$, —$N(CH_3)_2$, or —$NCH_3(CH_2CH_2OH)$; and $R^2$ represents ethyl, isopropyl, tert-butyl, methoxy, ethoxy, n-propoxy, isopropoxy, trifluoromethyl, difluoromethoxy, methylsulfonyl, or acetylamino; or X is CH, $R^1$ is hydrogen, and $R^2$ is ethyl, isopropyl, tert-butyl, ethoxy, n-propoxy, isopropoxy, methylsulfonyl, acetylamino, or methoxycarbonyl; or X is CH, $R^1$ is cyano, and $R^2$ is ethyl, isopropyl, tert-butyl, ethoxy, n-propoxy, isopropoxy, trifluoromethyl, difluoromethoxy, trifluoromethoxy, methylsulfonyl, or acetylamino; or X is CH, $R^1$ is chloro, and $R^2$ is ethyl, isopropyl, tert-butyl, ethoxy, n-propoxy, isopropoxy, difluoromethoxy, methylsulfonyl, or acetylamino; or X is CH, $R^1$ is methoxy or isopropoxy, and $R^2$ is trifluoromethyl.

iv) A further embodiment of the invention relates to compounds of the formula I according to embodiment i), wherein $R^1$ represents —$NO_2$, —$N(CH_3)_2$, or —$NCH_3(CH_2CH_2OH)$; and $R^2$ represents hydrogen, methyl, ethyl, n-propyl, isopropyl, tert-butyl, cyano, halogen, methoxy, ethoxy, n-propoxy, isopropoxy, trifluoromethyl, difluoromethoxy, methylsulfonyl, acetyl, or acetylamino.

v) A further embodiment of the invention relates to compounds of the formula I according to embodiment i), wherein $R^1$ represents —$NO_2$, —$N(CH_3)_2$, or —$NCH_3(CH_2CH_2OH)$; and $R^2$ represents ethyl, isopropyl, tert-butyl, methoxy, ethoxy, n-propoxy, isopropoxy, trifluoromethyl, difluoromethoxy, methylsulfonyl, or acetylamino.

vi) A further embodiment of the invention relates to compounds of the formula I according to embodiment iv) or v), wherein X is CH.

vii) A further embodiment of the invention relates to compounds of the formula I according to embodiment iv) or v), wherein X is N.

viii) A further embodiment of the invention relates to compounds of the formula I according to any one of embodiments iv) to vii), wherein $R^1$ represents —$NO_2$.

ix) A further embodiment of the invention relates to compounds of the formula I according to any one of embodiments iv) to vii), wherein $R^1$ represents —$N(CH_3)_2$.

x) A further embodiment of the invention relates to compounds of the formula I according to any one of embodiments iv) to vii), wherein $R^1$ represents —$NCH_3(CH_2CH_2OH)$.

xi) A further embodiment of the invention relates to compounds of the formula I according to any one of embodiments iv) to x), wherein $R^2$ is ethyl, isopropyl, tert-butyl, ethoxy, n-propoxy, or isopropoxy.

xii) A further embodiment of the invention relates to compounds of the formula I according to embodiment xi), wherein $R^2$ is isopropoxy.

xiii) A further embodiment of the invention relates to compounds of the formula I according to any one of embodiments iv) to x), wherein $R^2$ is trifluoromethyl, difluoromethoxy, methylsulfonyl, or acetylamino.

xiv) A further embodiment of the invention relates to compounds of the formula I according to any one of embodiments iv) to x), wherein $R^2$ is methoxy.

xv) A further embodiment of the invention relates to compounds of the formula I according to any one of embodiments iv) to x), wherein $R^2$ is hydrogen, methyl, n-propyl, cyano, halogen, or acetyl.

The term "halogen" as used herein means fluorine, chlorine, bromine or iodine, such as especially fluorine or chlorine.

Where the plural form is used for compounds, salts, pharmaceutical compositions, diseases and the like, this is intended to mean also a single compound, salt, or the like.

Any reference hereinbefore or hereinafter to a compound of formula I is to be understood as referring also to salts, especially pharmaceutically acceptable salts, of a compound of formula I, as appropriate and expedient.

The term "pharmaceutically acceptable salts" refers to non-toxic, inorganic or organic acid and/or base addition salts. Reference can be made to "Salt selection for basic drugs", *Int. J. Pharm.* 1986, 33, 201-17.

The present invention also includes isotopically labelled, especially $^2H$ (deuterium) labelled compounds of formula I, which compounds are identical to the compounds of formula I except that one or more atoms have each been replaced by an atom having the same atomic number but an atomic mass different from the atomic mass usually found in nature. Isotopically labelled, especially $^2H$ (deuterium) labelled compounds of formula I and salts thereof are within the scope of the present invention. Substitution of hydrogen with the heavier isotope $^2H$ (deuterium) may lead to greater metabolic stability, resulting e.g. in increased in vivo half-life or reduced dosage requirements, or may lead to reduced inhibition of cytochrome P450 enzymes, resulting e.g. in an improved safety profile. In one embodiment of the invention, the compounds of formula I are not isotopically labelled, or they are labelled only with one or more deuterium atoms. In a sub-embodiment, the compounds of formula I are not isotopically labelled at all. Isotopically labelled compounds of formula I may be prepared in analogy to the methods described hereinafter, but using the appropriate isotopic variation of suitable reagents or starting materials.

Examples of preferred compounds of formula I are selected from the group consisting of:

(S)—N-[4-(4-Acetyl-piperazin-1-yl)-benzyl]-N-{1-benzyl-2-[4-(4-dimethylamino-benzyl)-piperazin-1-yl]-2-oxo-ethyl}-3-(4-trifluoromethyl-phenyl)-acrylamide, (S)—N-[4-(4-Acetyl-piperazin-1-yl)-benzyl]-N-{1-benzyl-2-[4-(4-dimethylamino-benzyl)-piperazin-1-yl]-2-oxo-ethyl}-3-(6-trifluoromethyl-pyridin-3-yl)-acrylamide, (S)—N-[4-(4-Acetyl-piperazin-1-yl)-benzyl]-N-{1-benzyl-2-[4-(4-dimethylamino-benzyl)-piperazin-1-yl]-2-oxo-ethyl}-3-(6-methoxy-pyridin-3-yl)-acrylamide, (S)—N-[4-(4-Acetyl-piperazin-1-yl)-benzyl]-N-{1-benzyl-2-[4-(4-dimethylamino-benzyl)-piperazin-1-yl]-2-oxo-ethyl}-3-(6-ethoxy-pyridin-3-yl)-acrylamide, (S)—N-[4-(4-Acetyl-piperazin-1-yl)-benzyl]-N-{1-benzyl-2-[4-(4-dimethylamino-benzyl)-piperazin-1-yl]-2-oxo-ethyl}-3-(4-ethoxy-phenyl)-acrylamide, (S)—N-[4-(4-Acetyl-piperazin-1-yl)-benzyl]-N-{1-benzyl-2-[4-(4-dimethylamino-benzyl)-piperazin-1-yl]-2-oxo-ethyl}-3-(4-methanesulfonyl-phenyl)-acrylamide, (S)-3-(4-Acetylamino-phenyl)-N-[4-(4-acetyl-piperazin-1-yl)-benzyl]-N-{1-benzyl-2-[4-(4-dimethylamino-benzyl)piperazin-1-yl]-2-oxo-ethyl}-acrylamide, (S)—N-[4-(4-Acetyl-piperazin-1-yl)-benzyl]-N-{1-benzyl-2-[4-(4-dimethylamino-benzyl)-piperazin-1-yl]-2-oxo-ethyl}-3-(4-propoxy-phenyl)-acrylamide, (S)—N-[4-(4-Acetyl-piperazin-1-yl)-benzyl]-N-{1-benzyl-2-[4-(4-dimethylamino-benzyl)-piperazin-1-yl]-2-oxo-ethyl}-3-(4-isopropoxy-phenyl)-acrylamide, (S)—N-[4-(4-Acetyl-piperazin-1-yl)-benzyl]-N-{1-benzyl-2-[4-(4-dimethylamino-benzyl)-piperazin-1-yl]-2-oxo-ethyl}-3-(4-ethyl-phenyl)-acrylamide, (S)—N-[4-(4-Acetyl-piperazin-1-yl)-benzyl]-N-{1-benzyl-2-[4-(4-dimethylamino-benzyl)-piperazin-1-yl]-2-oxo-ethyl}-3-(4-difluoromethoxy-phenyl)-acrylamide, (S)—N-[4-(4-Acetyl-piperazin-1-yl)-benzyl]-N-{1-benzyl-2-[4-(4-dimethylamino-benzyl)-piperazin-1-yl]-2-oxo-ethyl}-3-(4-tert-butyl-phenyl)-acrylamide, (S)—N-[4-(4-Acetyl-piperazin-1-yl)-benzyl]-N-{1-benzyl-2-[4-(4-dimethylamino-benzyl)-piperazin-1-yl]-2-oxo-ethyl}-3-(4-isopropyl-phenyl)-acrylamide, (S)—N-[4-(4-Acetyl-piperazin-1-yl)-benzyl]-N-[1-benzyl-2-(4-{4-[(2-hydroxy-ethyl)-methyl-amino]-benzyl}-piperazin-1-yl)-2-oxo-ethyl]-3-(4-trifluoromethyl-phenyl)-acrylamide, (S)—N-[4-(4-Acetyl-piperazin-1-yl)-benzyl]-N-[1-benzyl-2-(4-{4-[(2-hydroxy-ethyl)-methyl-amino]-benzyl}-piperazin-1-yl)-2-oxo-ethyl]-3-(6-trifluoromethyl-pyridin-3-yl)-acrylamide, (S)—N-[4-(4-Acetyl-piperazin-1-yl)-benzyl]-N-[1-benzyl-2-(4-{4-[(2-hydroxy-ethyl)-methyl-amino]-benzyl}-piperazin-1-yl)-2-oxo-ethyl]-3-(6-methoxy-pyridin-3-yl)-acrylamide, (S)—N-[4-(4-Acetyl-piperazin-1-yl)-benzyl]-N-[1-benzyl-2-(4-{4-[(2-hydroxy-ethyl)-methyl-amino]-benzyl}-piperazin-1-yl)-2-oxo-ethyl]-3-(6-ethoxy-pyridin-3-yl)-acrylamide, (S)—N-[4-(4-Acetyl-piperazin-1-yl)-benzyl]-N-[1-benzyl-2-(4-{4-[(2-hydroxy-ethyl)-methyl-amino]-benzyl}-piperazin-1-yl)-2-oxo-ethyl]-3-(4-ethoxy-phenyl)-acrylamide, (S)—N-[4-(4-Acetyl-piperazin-1-yl)-benzyl]-N-[1-benzyl-2-(4-{4-[(2-hydroxy-ethyl)-methyl-amino]-benzyl}-piperazin-1-yl)-2-oxo-ethyl]-3-(4-methanesulfonyl-phenyl)-acrylamide, (S)-3-(4-Acetylamino-phenyl)-N-[4-(4-acetyl-piperazin-1-yl)-benzyl]-N-[1-benzyl-2-(4-{4-[(2-hydroxy-ethyl)-methyl-amino]-benzyl}-piperazin-1-yl)-2-oxo-ethyl]-acrylamide, (S)—N-[4-(4-Acetyl-piperazin-1-yl)-benzyl]-N-[1-benzyl-2-(4-{4-[(2-hydroxy-ethyl)-methyl-amino]-benzyl}-piperazin-1-yl)-2-oxo-ethyl]-3-(4-propoxy-phenyl)-acrylamide, (S)—N-[4-(4-Acetyl-piperazin-1-yl)-benzyl]-N-[1-benzyl-2-(4-{4-[(2-hydroxy-ethyl)-methyl-amino]-benzyl}-piperazin-1-yl)-2-oxo-ethyl]-3-(4-isopropoxy-phenyl)-acrylamide, (S)—N-[4-(4-Acetyl-piperazin-1-yl)-benzyl]-N-[1-benzyl-2-(4-{4-[(2-hydroxy-ethyl)-methyl-amino]-benzyl}-piperazin-1-yl)-2-oxo-ethyl]-3-(4-ethyl-phenyl)-acrylamide, (S)—N-[4-(4-Acetyl-piperazin-1-yl)-benzyl]-N-[1-benzyl-2-(4-{4-[(2-hydroxy-ethyl)-methyl-amino]-benzyl}-piperazin-1-yl)-2-oxo-ethyl]-3-(4-difluoromethoxy-phenyl)-acrylamide, (S)—N-[4-(4-Acetyl-piperazin-1-yl)-benzyl]-N-[1-benzyl-2-(4-{4-[(2-hydroxy-ethyl)-methyl-amino]-benzyl}-piperazin-1-yl)-2-oxo-ethyl]-3-(4-isopropyl-phenyl)-acrylamide, (S)—N-[4-(4-Acetyl-piperazin-1-yl)-benzyl]-N-[1-benzyl-2-(4-{4-[(2-hydroxy-ethyl)-methyl-amino]-benzyl}-piperazin-1-yl)-2-oxo-ethyl]-3-(4-tert-butyl-phenyl)-acrylamide, and (S)—N-[4-(4-Acetyl-piperazin-1-yl)-benzyl]-N-{1-benzyl-2-[4-(4-nitro-benzyl)-piperazin-1-yl]-2-oxo-ethyl}-3-(4-trifluoromethyl-phenyl)-acrylamide.

Further examples of preferred compounds of formula I are selected from the group consisting of:

(S)—N-[4-(4-Acetyl-piperazin-1-yl)benzyl]-N-{1-(4-(4-(dimethylamino)benzyl)piperazin-1-yl)-1-oxo-3-phenylpropan-2-yl}cinnamamide, (S)—N-[4-(4-Acetyl-piperazin-1-yl)benzyl]-N-{1-[4-(4-(dimethylamino)benzyl)piperazin-1-yl]-1-oxo-3-phenylpropan-2-yl}-3-(p-tolyl)acrylamide, (S)—N-[4-(4-Acetyl-piperazin-1-yl)benzyl]-N-{1-(4-(4-(dimethylamino)benzyl)piperazin-1-yl)-1-oxo-3-phenylpropan-2-yl}-3-(4-propylphenyl)acrylamide, (S)—N-[4-(4-Acetyl-piperazin-1-yl)benzyl]-N-{1-(4-(4-(dimethylamino)benzyl)piperazin-1-yl)-1-oxo-3-phenylpropan-2-yl}-3-(4-methoxyphenyl)acrylamide, (S)-3-(4-Acetyl-phenyl)-N-[4-(4-acetyl-piperazin-1-yl)benzyl]-N-{1-(4-(4-(dimethylamino)benzyl)piperazin-1-yl)-1-oxo-3-phenylpropan-2-yl}acrylamide, (S)—N-[4-(4-Acetyl-piperazin-1-yl)benzyl]-3-(4-cyanophenyl)-N-{1-(4-(4-(dimethylamino)benzyl)piperazin-1-yl)-1-oxo-3-phenylpropan-2-yl}acrylamide, (S)—N-[4-(4-Acetyl-piperazin-1-yl)benzyl]-N-{1-(4-(4-(dimethylamino)benzyl)piperazin-1-yl)-1-oxo-3-phenylpropan-2-yl}-3-(4-fluorophenyl)acrylamide, and (S)—N-[4-(4-Acetyl-piperazin-1-yl)benzyl]-3-(4-chlorophenyl)-N-{1-(4-(4-(dimethylamino)benzyl)piperazin-1-yl)-1-oxo-3-phenylpropan-2-yl}acrylamide.

Further examples of preferred compounds of formula I are selected from the group consisting of:

(S)—N-[4-(4-Acetyl-piperazin-1-yl)-benzyl]-N-[1-benzyl-2-(4-benzyl-piperazin-1-yl)-2-oxo-ethyl]-3-(4-ethyl-phenyl)-acrylamide, (S)—N-[4-(4-Acetyl-piperazin-1-yl)-benzyl]-N-[1-benzyl-2-(4-benzyl-piperazin-1-yl)-2-oxo-ethyl]-3-(4-tert-butyl-phenyl)-acrylamide, (S)—N-[4-(4-Acetyl-piperazin-1-yl)-benzyl]-N-[1-benzyl-2-(4-benzyl-piperazin-1-yl)-2-oxo-ethyl]-3-(4-ethoxy-phenyl)-acrylamide, (S)-4-(2-{[4-(4-Acetyl-piperazin-1-yl)-benzyl]-[1-benzyl-2-(4-benzyl-piperazin-1-yl)-2-oxo-ethyl]carbamoyl}-vinyl)-benzoic acid methyl ester, (S)—N-[4-(4-Acetyl-piperazin-1-yl)-benzyl]-N-[1-benzyl-2-(4-benzyl-piperazin-1-yl)-2-oxo-ethyl]-3-(4-methanesulfonyl-phenyl)-acrylamide, (S)-3-(4-Acetylamino-phenyl)-N-[4-(4-acetyl-piperazin-1-yl)-benzyl]-N-[1-benzyl-2-(4-benzyl-piperazin-1-yl)-2-oxo-ethyl]-acrylamide, (S)—N-[4-(4-Acetyl-piperazin-1-yl)-benzyl]-N-[1-benzyl-2-(4-benzyl-piperazin-1-yl)-2-oxo-ethyl]-3-(4-propoxy-phenyl)acrylamide, (S)—N-[4-(4-Acetyl-piperazin-1-yl)-benzyl]-N-[1-benzyl-2-(4-benzyl-piperazin-1-yl)-2-oxo-ethyl]-3-(4-isopropoxy-phenyl)-acrylamide, (S)—N-[4-(4-Acetyl-piperazin-1-yl)-benzyl]-N-[1-benzyl-2-(4-benzyl-piperazin-1-yl)-2-oxo-ethyl]-3-(4-isopropyl-phenyl)-acrylamide, (S)—N-[4-(4-Acetyl-piperazin-1-yl)-benzyl]-N-{1-benzyl-2-[4-(4-cyano-benzyl)-piperazin-1-yl]-2-oxo-ethyl}-3-(4-trifluoromethyl-phenyl)-acrylamide, (S)—N-[4-(4-Acetyl-piperazin-1-yl)-benzyl]-N-{1-benzyl-2-[4-(4-cyano-benzyl)-piperazin-1-yl]-2-oxo-ethyl}-3-(4-ethoxy-phenyl)-acrylamide, (S)—N-[4-(4-Acetyl-piperazin-1-yl)-benzyl]-N-{1-benzyl-2-[4-(4-cyano-benzyl)-piperazin-1-yl]-2-oxo-ethyl}-3-(4-methanesulfonyl-phenyl)acrylamide, (S)-3-(4-Acetylamino-phenyl)-N-[4-(4-acetyl-piperazin-1-yl)-benzyl]-N-{1-benzyl-2-[4-(4-cyano-benzyl)-piperazin-1-yl]-2-oxo-ethyl}-acrylamide, (S)—N-[4-(4-Acetyl-piperazin-1-yl)-benzyl]-N-{1-benzyl-2-[4-(4-cyano-benzyl)-piperazin-1-yl]-2-oxo-ethyl}-3-(4-propoxy-phenyl)-acrylamide, (S)—N-[4-(4-Acetyl-piperazin-1-yl)-benzyl]-N-{1-benzyl-2-[4-(4-cyano-benzyl)-piperazin-1-yl]-2-oxo-ethyl}-3-(4-isopropoxy-phenyl)-acrylamide, (S)—N-[4-(4-Acetyl-piperazin-1-yl)-benzyl]-N-{1-benzyl-2-[4-(4-cyano-benzyl)-piperazin-1-yl]-2-oxo-ethyl}-3-(4-ethyl-phenyl)-acrylamide, (S)—N-[4-(4-Acetyl-piperazin-1-yl)-benzyl]-N-{1-benzyl-2-[4-(4-cyano-benzyl)-piperazin-1-yl]-2-oxo-ethyl}-3-(4-difluoromethoxy-phenyl)-acrylamide, (S)—N-[4-(4-Acetyl-piperazin-1-yl)-benzyl]-N-{1-benzyl-2-[4-(4-cyano-benzyl)-piperazin-1-yl]-2-oxo-ethyl}-3-(4-isopropyl-phenyl)-acrylamide, (S)—N-[4-(4-Acetyl-piperazin-1-yl)-benzyl]-N-{1-benzyl-2-[4-(4-cyano-benzyl)-piperazin-1-yl]-2-oxo-ethyl}-3-(4-trifluoromethoxy-phenyl)-acrylamide, (S)—N-[4-(4-Acetyl-piperazin-1-yl)-benzyl]-N-{1-benzyl-2-[4-(4-cyano-benzyl)-piperazin-1-yl]-2-oxo-ethyl}-3-(4-tert-butyl-phenyl)-acrylamide, (S)—N-[4-(4-Acetyl-piperazin-1-yl)-benzyl]-N-{1-benzyl-2-[4-(4-chloro-benzyl)-piperazin-1-yl]-2-oxo-ethyl}-3-(4-ethoxy-phenyl)-acrylamide, (S)—N-[4-(4-Acetyl-piperazin-1-yl)-benzyl]-N-{1-benzyl-2-[4-(4-chloro-benzyl)-piperazin-1-yl]-2-oxo-ethyl}-3-(4-methanesulfonyl-phenyl)acrylamide, (S)-3-(4-Acetylamino-phenyl)-N-[4-(4-acetyl-piperazin-1-yl)-benzyl]-N-{1-benzyl-2-[4-(4-chloro-benzyl)-piperazin-1-yl]-2-oxo-ethyl}-acrylamide, (S)—N-[4-(4-Acetyl-piperazin-1-yl)-benzyl]-N-{1-benzyl-2-[4-(4-chloro-benzyl)-piperazin-1-yl]-2-oxo-ethyl}-3-(4-propoxy-phenyl)-acrylamide, (S)—N-[4-(4-Acetyl-piperazin-1-yl)-benzyl]-N-{1-benzyl-2-[4-(4-chloro-benzyl)-piperazin-1-yl]-2-oxo-ethyl}-3-(4-isopropoxy-phenyl)-acrylamide, (S)—N-[4-(4-Acetyl-piperazin-1-yl)-benzyl]-N-{1-benzyl-2-[4-(4-chloro-benzyl)-piperazin-1-yl]-2-oxo-ethyl}-3-(4-ethyl-phenyl)-acrylamide, (S)—N-[4-(4-Acetyl-piperazin-1-yl)-benzyl]-N-{1-benzyl-2-[4-(4-chloro-benzyl)-piperazin-1-yl]-2-oxo-ethyl}-3-(4-difluoromethoxy-phenyl)-acrylamide, (S)—N-[4-(4-Acetyl-piperazin-1-yl)-benzyl]-N-{1-benzyl-2-[4-(4-chloro-benzyl)-piperazin-1-yl]-2-oxo-ethyl}-3-(4-isopropyl-phenyl)-acrylamide, (S)—N-[4-(4-Acetyl-piperazin-1-yl)-benzyl]-N-{1-benzyl-2-[4-(4-chloro-benzyl)-piperazin-1-yl]-2-oxo-ethyl}-3-(4-tert-butyl-phenyl)-acrylamide, (S)—N-[4-(4-Acetyl-piperazin-1-yl)-benzyl]-N-{1-benzyl-2-[4-(4-methoxy-benzyl)-piperazin-1-yl]-2-oxo-ethyl}-3-(4-trifluoromethyl-phenyl)-acrylamide, and (S)—N-[4-(4-Acetyl-piperazin-1-yl)-benzyl]-N-{1-benzyl-2-[4-(4-isopropoxy-benzyl)-piperazin-1-yl]-2-oxo-ethyl}-3-(4-trifluoromethyl-phenyl)-acrylamide.

Further examples of preferred compounds of formula I are selected from the group consisting of:

(S)—N-[4-(4-Acetyl-piperazin-1-yl)-benzyl]-N-{1-benzyl-2-[4-(4-(methylsulfonyl)-benzyl)-piperazin-1-yl]-2-oxo-ethyl}-3-(4-isopropoxyphenyl)-acrylamide, (S)—N-[4-(4-Acetyl-piperazin-1-yl)-benzyl]-N-{1-benzyl-2-[4-(4-(methylsulfonyl)-benzyl)-piperazin-1-yl]-2-oxo-ethyl}-3-(4-tert-butyl-phenyl)-acrylamide, (S)—N-[4-(4-Acetyl-piperazin-1-yl)-benzyl]-N-{1-benzyl-2-[4-(4-(methylsulfonyl)-benzyl)-piperazin-1-yl]-2-oxo-ethyl}-3-(4-propoxyphenyl)-acrylamide, (S)—N-(4-(4-acetylpiperazin-1-yl)benzyl)-N-(1-(4-(4-(methylsulfonyl)benzyl)piperazin-1-yl)-1-oxo-3-phenylpropan-2-yl)-3-(4-(trifluoromethyl)phenyl)acrylamide, (S)—N-[4-(4-Acetyl-piperazin-1-yl)-benzyl]-N-{1-benzyl-2-[4-(4-(ethylsulfonyl)-benzyl)-piperazin-1-yl]-2-oxo-ethyl}-3-(4-propoxyphenyl)-acrylamide, and (S)—N-(4-(4-acetylpiperazin-1-yl)benzyl)-N-(1-(4-(4-(ethylsulfonyl)benzyl)piperazin-1-yl)-1-oxo-3-phenylpropan-2-yl)-3-(4-(trifluoromethyl)phenyl)acrylamide.

The compounds of formula I and their pharmaceutically acceptable salts can be used as medicaments, e.g. in the form of pharmaceutical compositions for enteral or parenteral administration, and are suitable for the treatment and/or prevention of the diseases mentioned herein, such as especially malaria.

The production of the pharmaceutical compositions can be effected in a manner which will be familiar to any person skilled in the art (see for example Remington, *The Science and Practice of Pharmacy,* 21st Edition (2005), Part 5, "Pharmaceutical Manufacturing" [published by Lippincott Williams & Wilkins]) by bringing the described compounds of formula I or their pharmaceutically acceptable salts, optionally in combination with other therapeutically valuable substances, into a galenical administration form together with suitable, non-toxic, inert, pharmaceutically acceptable solid or liquid carrier materials and, if desired, usual pharmaceutical adjuvants.

In one embodiment, the invention relates to a method for the treatment or prevention of the diseases mentioned herein, such as especially malaria, said method comprising administering to a subject a pharmaceutically active amount of a compound of formula I.

The compounds of formula I or the above-mentioned pharmaceutical compositions may also be used in combination with one or more other therapeutically useful substances e.g. with other antimalarials like quinolines (e.g. quinine, chloroquine, amodiaquine, mefloquine, primaquine, and tafenoquine), peroxide antimalarials (e.g. artemisinin, artemether, and artesunate), pyrimethamine-sulfadoxine antimalarials (e.g. Fansidar®), hydroxynaphtoquinones (e.g. atovaquone), acroline-type antimalarials (e.g. pyronaridine), and other antiprotozoal agents like ethylstibamine, hydroxystilbamidine, pentamidine, stilbamidine, quinapyramine, puromycine, propamidine, nifurtimox, melarsoprol, nimorazole, nifuroxime, aminitrozole and the like.

The present invention also relates to the use of a compound of formula I for the preparation of a pharmaceutical composition, optionally for use in combination with one or more other therapeutically useful substances such as those mentioned in the preceding paragraph, for the prevention and/or treatment of the diseases mentioned herein, such as especially malaria.

The compounds of the formula I of the present invention may be prepared according to the procedures described herein, especially as described in the experimental part.

In general, all chemical transformations can be performed according to well-known standard methodologies as described in the literature or as described in the procedures below.

Preparation of compounds of formula I, except for compounds wherein $R^1$ is —$NCH_3(CH_2CH_2OH)$:
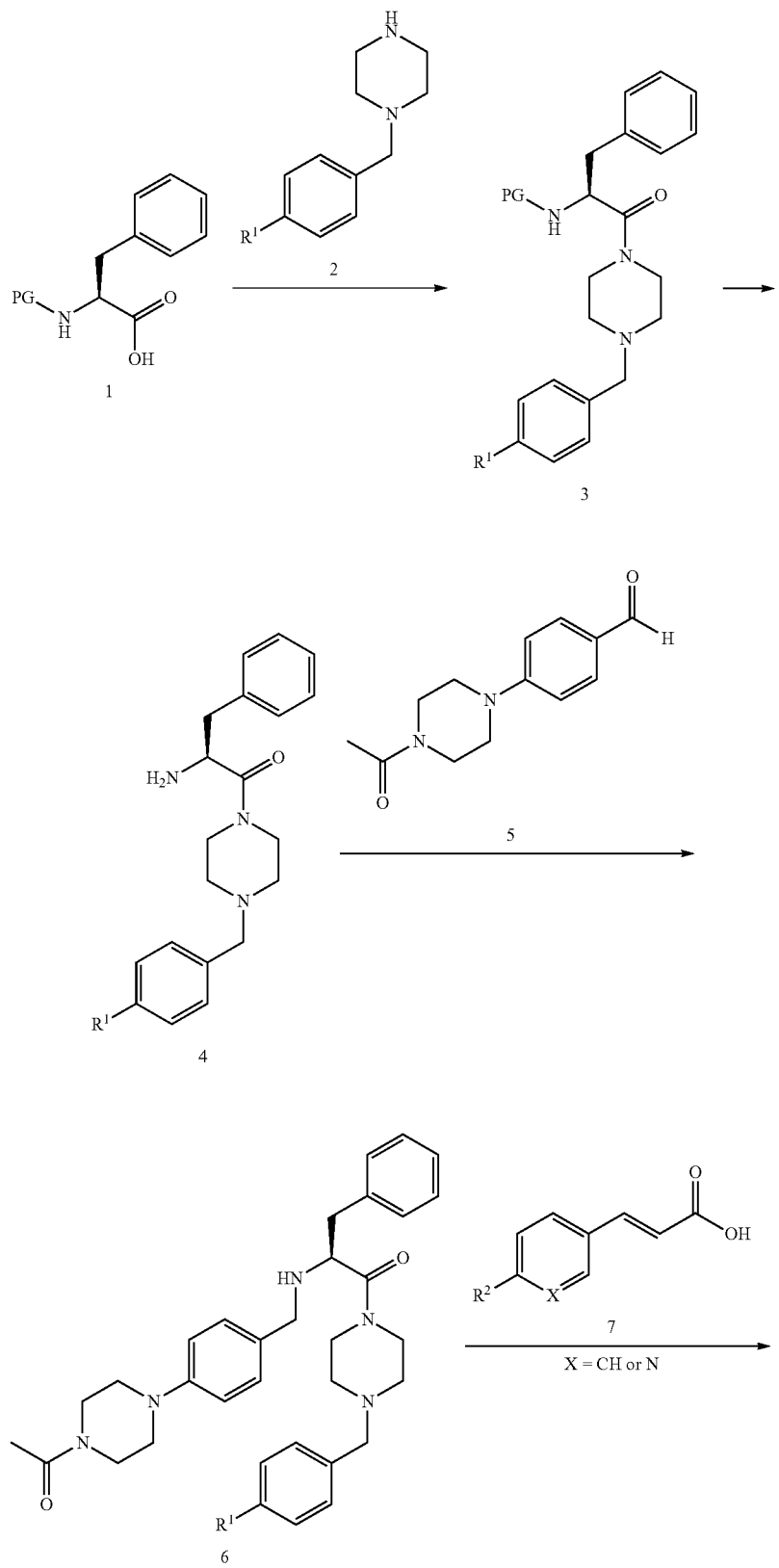
Scheme 1

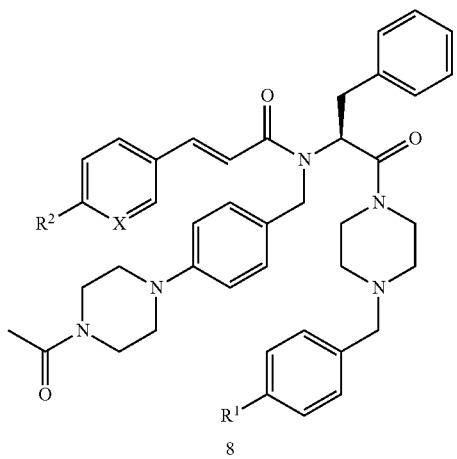

8

The Boc-Phe-OH 1 can be coupled with the benzylpiperazine derivative 2 via a peptidic coupling using activating agents such as TBTU (or PyBOP/HOBt) in the presence of a base such as DIPEA (or NEM) in DCM (or DMF) at RT to afford the intermediate 3. Alternatively, Cbz-Phe-OH can also be used in the initial peptidic coupling step to give 3. Boc-deprotection is usually achieved by reacting 3 with a solution of HCl 4N in dioxane using DCM as solvent, while Cbz-deprotection is achieved by hydrogenation with Pd/C catalyst in MeOH, to give the amine intermediate 4. Reductive amination between the free amine 4 and the aldehyde 5 at reflux in MeOH afforded the unstable imine (not depicted in the scheme), which is further reduced at RT with NaBH₄ to give the secondary amine intermediate 6. Alternatively, the reductive amination can be achieved in a solvent such as CH₃CN in the presence of a reducing reagent such as NaBH(OAc)₃ to give the expected secondary amine intermediate 6. Compound 6 can then be coupled with a carboxylic acid 7 using a peptidic coupling reagent such as TBTU, PyBOP/HOBt or the Ghosez's reagent in a solvent such as DCM (or DMF) at RT in the presence of a base such as DIPEA (or NEM). Alternatively, the carboxylic acid 7 can be converted to the corresponding acid chloride (not depicted in the scheme) using oxalyl chloride in DCM to give the final compounds 8 of formula I.

When R¹=—NCH₃(CH₂CH₂OH) the compounds of formula I are prepared according to Scheme 2.

Scheme 2

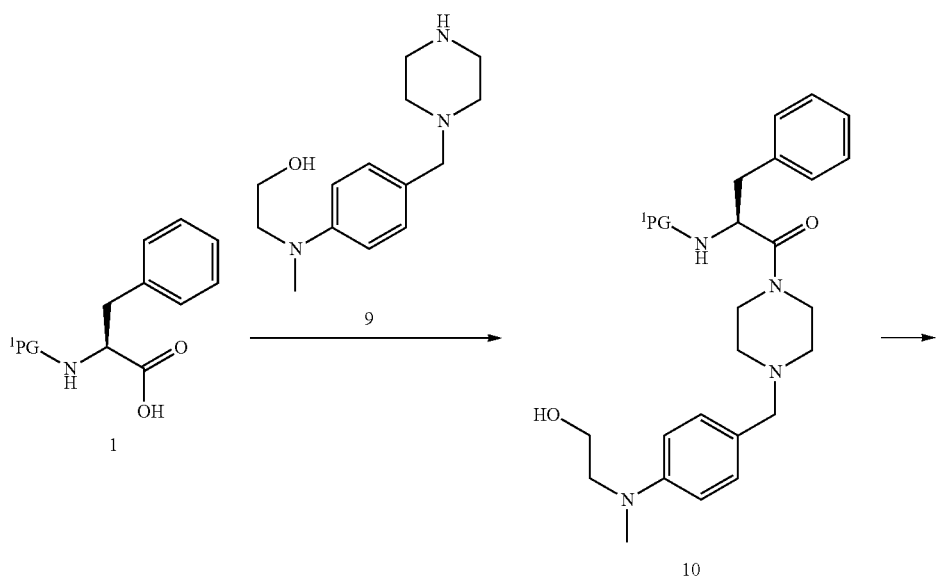

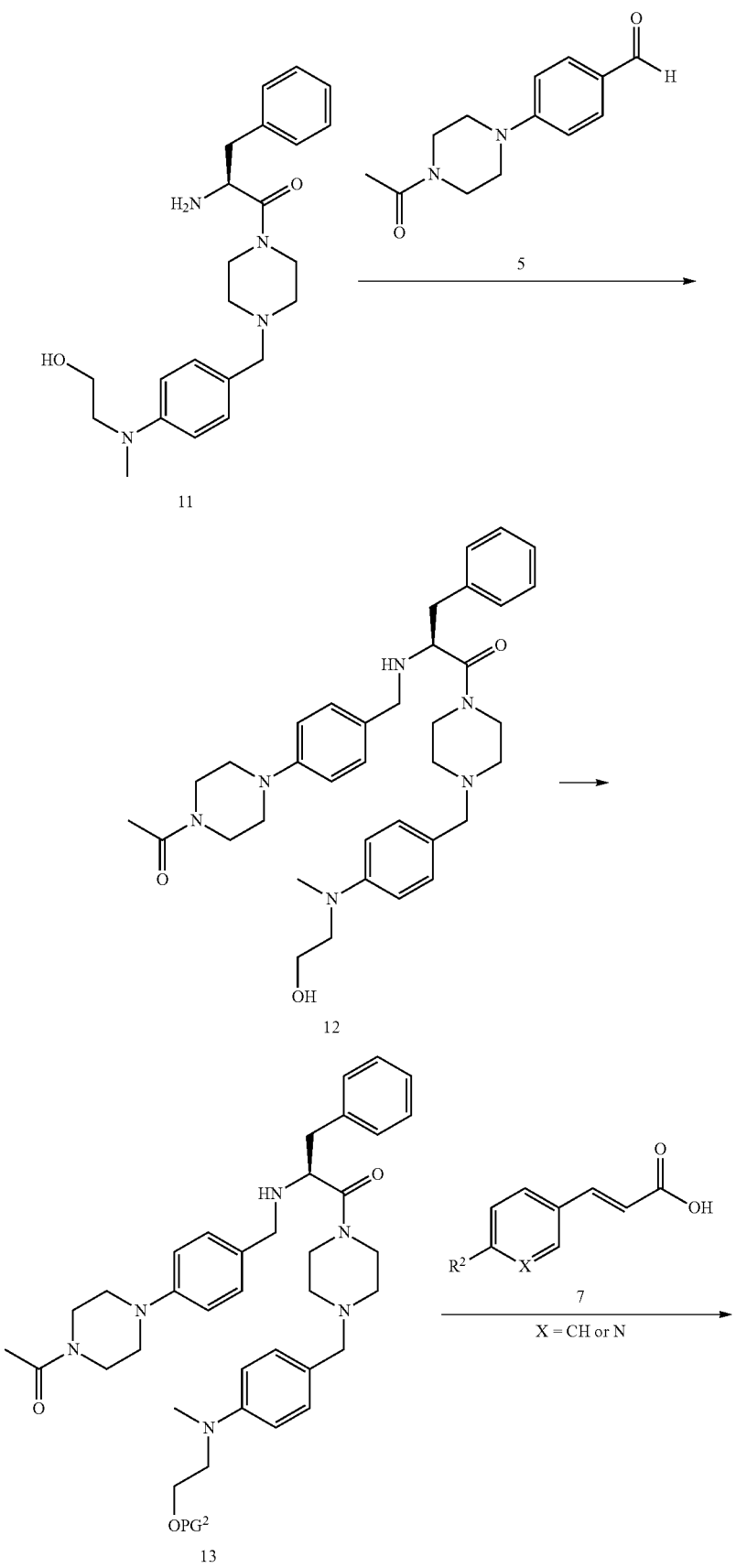

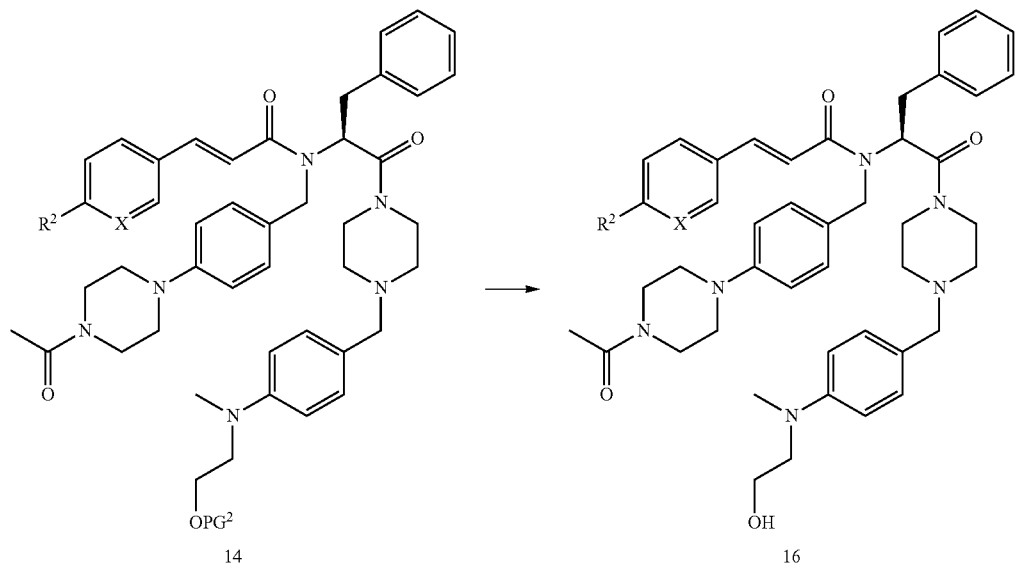

The Boc-Phe-OH 1 is coupled with the benzylpiperazine derivative 9 via a peptidic coupling reaction using activating agents such as TBTU (or PyBOP/HOBt) in the presence of a base such as DIPEA (or NEM) in DCM (or DMF) at RT to afford the intermediate 10. Alternatively, Cbz-Phe-OH can also be used in the initial peptide coupling step to give 10. Boc-deprotection is usually achieved by reacting 10 with a solution of HCl 4N in dioxane using DCM as solvent, while Cbz-deprotection is achieved by hydrogenation with Pd/C catalyst in MeOH, to give the amine intermediate 11. Reductive amination between the free amine 11 and the aldehyde 5 in $CH_3CN$ at RT in the presence of a reducing agent such as $NaBH(OAc)_3$ affords the secondary amine intermediate 12. The free hydroxyl group of compound 12 is protected using for instance TBDMSCl as silylating agent to give 13, which is then coupled with a carboxylic acid 7 using a peptide coupling reagent such as TBTU (or PyBOP/HOBt) in a solvent such as DCM (or DMF) at RT in the presence of a base such as DIPEA. Alternatively, the carboxylic acid 7 can be activated by converting it to the corresponding acid chloride (not depicted in the scheme) using oxalyl chloride in DCM, to subsequently give compound 14. Further deprotection under mild acidic conditions such as aqueous 1 M HCl in MeOH or fluorinated reagents such as TBAF yield the final compounds 16 of formula I.

The compounds of formula I can also be prepared according to the pathway depicted in Scheme 3.

Scheme 3

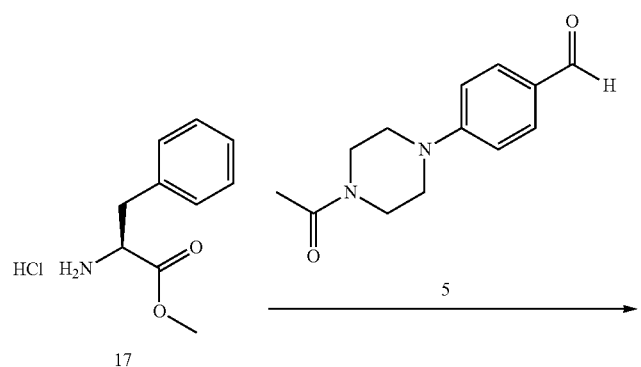

-continued
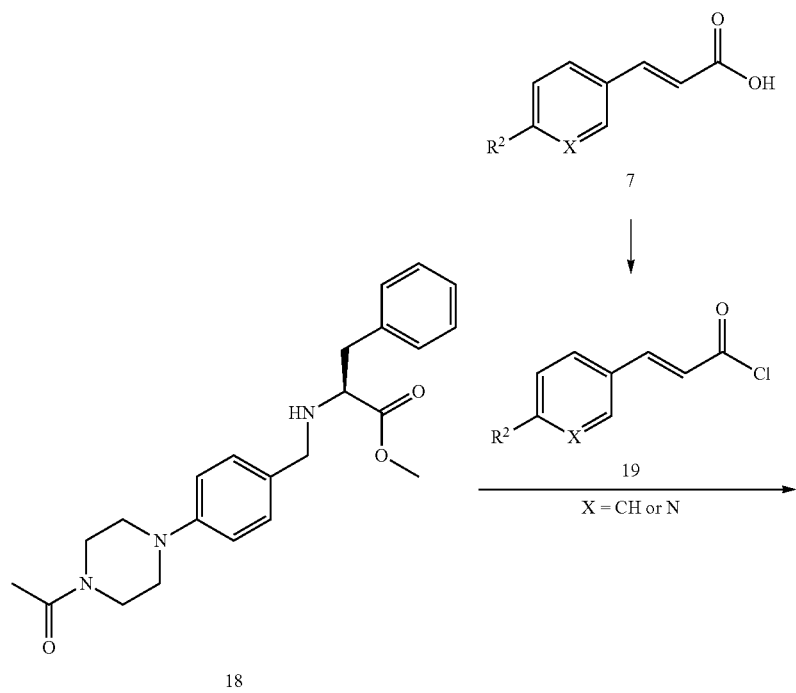
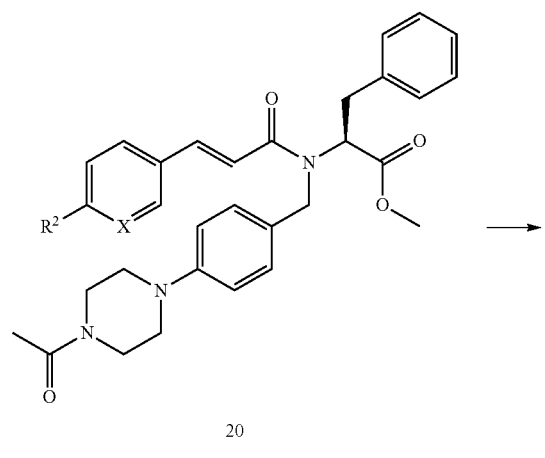
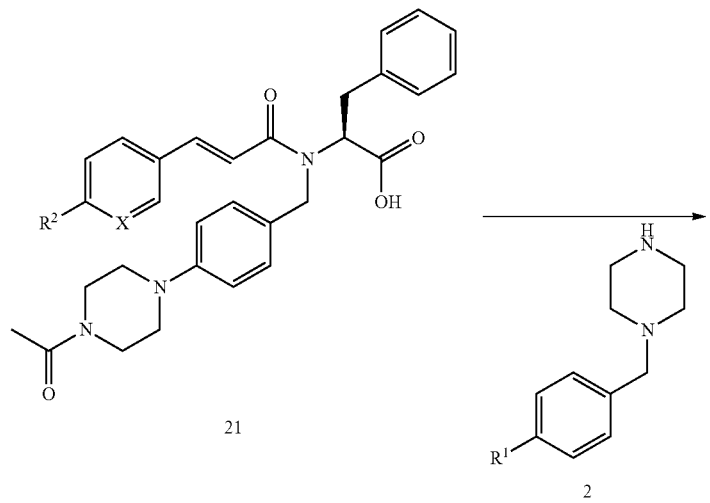

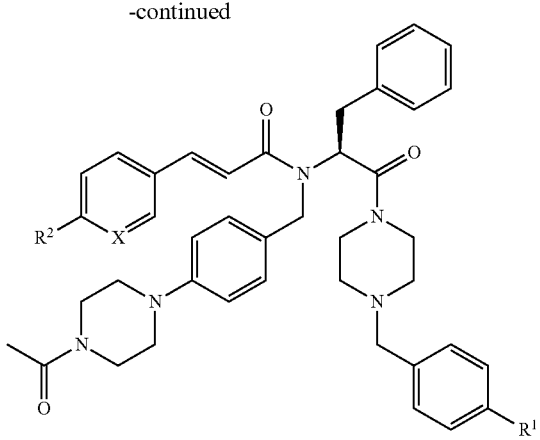

8

Reductive amination between the amino acid H-Phe-OMe-.HCl 17 and the aldehyde 5 in MeOH under reflux affords the corresponding imine, which is further reduced to the secondary amine 18 in the presence of a reducing reagent such as NaBH$_4$ at RT. 18 can also be obtained using the conditions described above for compounds 6 and 12. The ester 18 is then coupled with the acid chloride 19 derived from the carboxylic acid 7 using oxalyl chloride in DCM or Ghosez's reagent. Alternatively, 18 can be directly coupled with the carboxylic acid 7 via a peptide coupling reaction using TBTU (or PyBOP/HOBt) as coupling agents in a solvent such as DCM (or DMF) at RT in the presence of a base such as DIPEA (or NEM). Careful saponification of the ester 20 with aqueous LiOH 0.5 N in THF at 0° C. affords the acid 21. Final peptide coupling with the benzylpiperazine 2 gives the final compounds 8 of formula I.

Benzylpiperazines 2 and 9 are commercially available and/or can be synthesized according to the following synthetic Scheme 4:

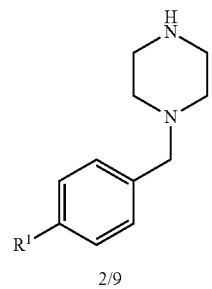

2/9

Cinnamic acids 7 are commercially available or/and can be synthesized according to the following pathways:

Pathway A: Knoevenagel Reaction

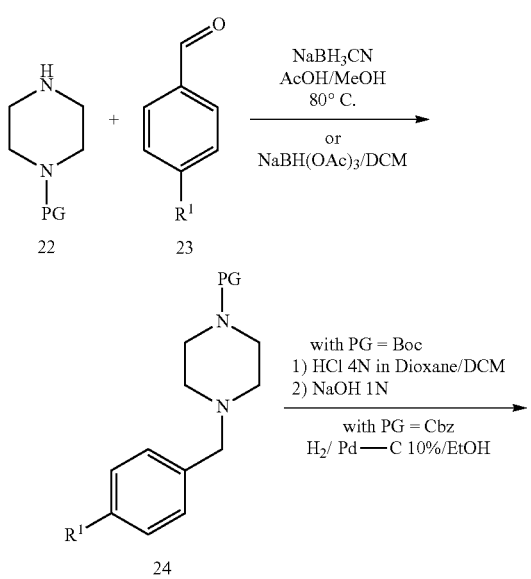

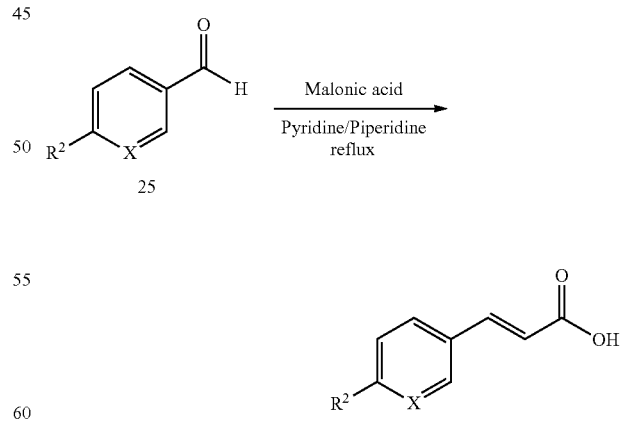

The cinnamic acids 7 are obtained by refluxing the aldehyde 25 with malonic acid in a mixture of piperidine/pyridine (WO 00/66566).

Pathway B: Horner-Emmons Reaction

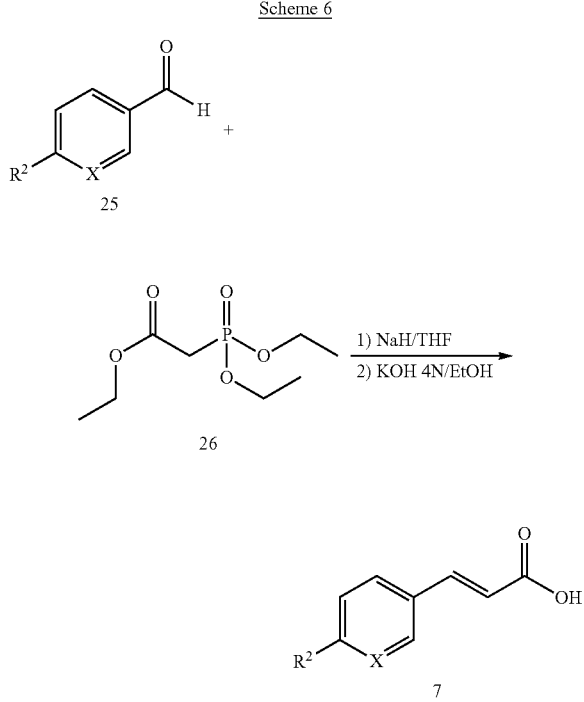

Scheme 6

The cinnamic acids 7 are obtained in two steps by reacting the aldehydes 25 with triethyl phosphoacetate 26 in the presence of a base such as NaH in an aprotic solvent such as THF followed by saponification of the resulting ethyl ester with 4 N KOH in EtOH.

The following examples illustrate the present invention. All temperatures are stated in degrees Celsius and pressures in mbar. Unless mentioned otherwise, the reactions take place at RT. The ratio of amounts of solvents to one another is always stated in parts by volume. Chemical names for final products and intermediates have been generated on the basis of the chemical structural formulae with the aid of Chem-DrawPro Automatic Nomenclature program.

Analytic HPLC Conditions:

(I) Agilent 1100 series with UV/Vis and MS detection (MS: Thermo Finnigan single quadrupole). Columns (4.6×50 mm, 5 μm): Waters X-Bridge C18 or Waters Atlantis T3.

Basic conditions: eluents: A: MeCN, B: concentrated $NH_3$ in water (1.0 mL/L). Gradient 5 to 95% A over 1.5 min. Flow rate: 4.5 mL/min.

Acidic conditions: eluents A: water+0.04% TFA, B: MeCN. Gradient 5 to 95% over 1.5 min. Flow rate 4.5 mL/min.

Preparative HPLC Conditions:

Gilson with UV/Vis+MS or UV/Vis+ELSD detection. Basic conditions: eluents: A: MeCN, B: $H_2O$+0.5% $NH_3$ (25% aqueous).

(II) Waters X-Bridge column, 19×50 mm, 5 μm. Gradient: 20 to 90% A over 5 min. Flow rate: 40 mL/min.

(III) Waters X-Bridge column, 30×75 mm, 10 μm. Gradient: 20 to 90% A over 6 min. Flow rate: 75 mL/min.

The following abbreviations are used herein:

AcOH acetic acid
Boc tert.-butyloxycarbonyl
Boc-Phe-OH Boc-L-phenylanaline
Cbz benzyloxycarbonyl
Cbz-Phe-OH Cbz-L-phenylanaline
DCM dichloromethane
DIPEA N,N-diisopropylethylamine
DMF N,N-dimethylformamide
Et ethyl
EtOH ethanol
EtOAc ethyl acetate
$Et_2O$ diethylether
ELSD evaporative light scattering detection
h hour(s)
HOBt hydroxybenzotriazole
H-Phe-OMe.HCl L-phenylalanine methylester hydrochloride
HPLC high performance liquid chromatography
LC-MS liquid chromatography-mass spectroscopy
Me methyl
MeOH methanol
min minute(s)
MS mass spectroscopy
$NaBH(OAc)_3$ sodium triacetoxyborohydride
NEM N-ethyl morpholine
PBS phosphate buffered saline
Pd/C palladium on carbon
PG protecting group
PyBOP benzotriazol-1-yl-oxy-tris-pyrrolidinophosphonium hexafluorophosphate
quant. quantitative
RT room temperature
Rt retention time of a substance in HPLC (in minutes)
TBAF tetra-n-butylammonium fluoride
TBDMSCl tert-butyldimethyl chlorosilane
TBTU O-benzotriazol-1-yl-N,N,N',N'-tetramethyluronium tetrafluoroborate
TFA trifluoroacetic acid
THF tetrahydrofuran
UV ultra violet
V is visible
number

| The following abbreviations are used herein: | |
|---|---|
| AcOH | acetic acid |
| Boc | tert.-butyloxycarbonyl |
| Boc-Phe-OH | Boc-L-phenylanaline |
| Cbz | benzyloxycarbonyl |
| Cbz-Phe-OH | Cbz-L-phenylanaline |
| DCM | dichloromethane |
| DIPEA | N,N-diisopropylethylamine |
| DMF | N,N-dimethylformamide |
| Et | ethyl |
| EtOH | ethanol |
| EtOAc | ethyl acetate |
| $Et_2O$ | diethylether |
| ELSD | evaporative light scattering detection |
| h | hour(s) |
| HOBt | hydroxybenzotriazole |
| H—Phe-OMe•HCl | L-phenylalanine methylester hydrochloride |
| HPLC | high performance liquid chromatography |
| LC-MS | liquid chromatography-mass spectroscopy |
| Me | methyl |
| MeOH | methanol |
| min | minute(s) |
| MS | mass spectroscopy |

The following abbreviations are used herein:

| | |
|---|---|
| NaBH(OAc)$_3$ | sodium triacetoxyborohydride |
| NEM | N-ethyl morpholine |
| PBS | phosphate buffered saline |
| Pd/C | palladium on carbon |
| PG | protecting group |
| PyBOP | benzotriazol-1-yl-oxy-tris-pyrrolidinophosphonium hexafluorophosphate |
| quant. | quantitative |
| RT | room temperature |
| Rt | retention time of a substance in HPLC (in minutes) |
| TBAF | tetra-n-butylammonium fluoride |
| TBDMSCl | tert-butyldimethyl chlorosilane |
| TBTU | O-benzotriazol-1-yl-N,N,N',N'-tetramethyluronium tetrafluoroborate |
| TFA | trifluoroacetic acid |
| THF | tetrahydrofuran |
| UV | ultra violet |
| Vis | visible |
| # | number |

Preparation of Compounds of Formula I Via Pathway Depicted in Scheme 1

General Procedures and Examples

General Method A—Step 1

Scheme 7

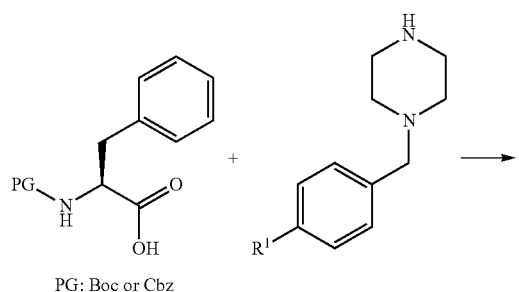

PG: Boc or Cbz

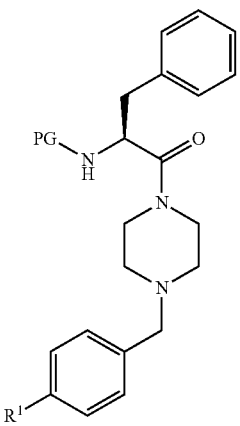

To a stirred suspension of 1 mmol of Boc-Phe-OH or Cbz-Phe-OH in 0.6 mL of dry DCM (or DMF) under nitrogen are successively added 1 mmol of TBTU and 2 mmol of NEM. The resulting light yellow suspension is stirred at RT for 1 h before a solution of 1 mmol of benzylpiperazine in 0.25 mL of dry DCM (or DMF) is added. The obtained reaction mixture is further stirred at RT overnight. Upon completion the reaction is diluted with DCM and quenched with a saturated solution of NaHCO$_3$. The aqueous phase is extracted with DCM (×3), the combined organic phases are successively washed with H$_2$O and brine, dried over Na$_2$SO$_4$, filtered and concentrated under reduced pressure. The residue is purified by flash chromatography (SiO$_2$ 60F) to afford the title compound.

Intermediates 1

| | | | LC-MS | |
|---|---|---|---|---|
| R$^1$/PG | Chemical name | Yield | Rt (min) | [M + H]$^+$ |
| H/Boc | (S)-[1-Benzyl-2-(4-benzyl-piperazin-1-yl)-2-oxo-ethyl]-carbamic acid tert-butyl ester | Quant. | 0.98* | 424.22 |
| CN/Boc | (S)-{1-Benzyl-2-[4-(4-cyano-benzyl)-piperazin-1-yl]-2-oxo-ethyl}-carbamic acid tert-butyl ester | 94% | 0.92* | 449.12 |
| N(CH$_3$)$_2$/Boc | (S)-{1-Benzyl-2-[4-(4-dimethylamino-benzyl)-piperazin-1-yl]-2-oxo-ethyl}-carbamic acid tert-butyl ester | Quant. | 0.96* | 467.23 |
| Cl/Boc | (S)-{1-Benzyl-2-[4-(4-chloro-benzyl)-piperazin-1-yl]-2-oxo-ethyl}-carbamic acid tert-butyl ester | Quant. | 1.01* | 457.79 |
| S(O$_2$)Me/Cbz | (S)-Benzyl (1-(4-(4-(methylsulfonyl)benzyl)piperazin-1-yl)-1-oxo-3-phenylpropan-2-yl)carbamate | 76% | 0.62** | 536.16 |
| S(O$_2$)Et/Cbz | (S)-Benzyl (1-(4-(4-(ethylsulfonyl)benzyl)piperazin-1-yl)-1-oxo-3-phenylpropan-2-yl)carbamate | 47% | 0.64** | 550.17 |

*Analytic I, X-Bridge column, basic conditions.
**Analytic, Waters Atlantis T3 column, acidic conditions

General Method B—Step 2

Scheme 8

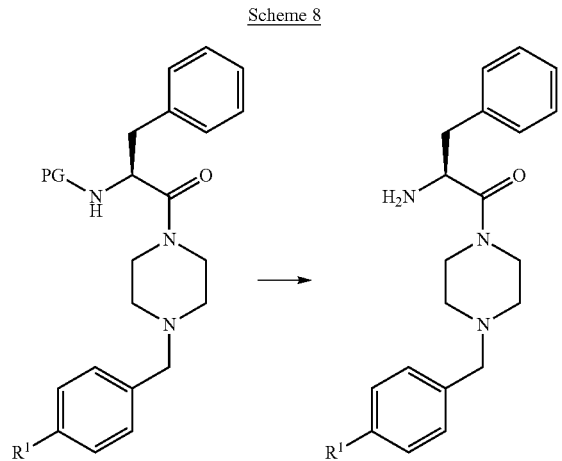

With PG=Boc:

To a solution of 1 mmol of the Boc-protected amine in 9 mL of dry DCM at 0° C. are added dropwise 4.5 mL of HCl 4N in dioxane. The resulting reaction mixture is stirred at RT for 4 h under nitrogen atmosphere, cooled down to 0° C. and carefully neutralized to pH=7 with an aqueous solution of NaOH 1N. The aqueous phase is then extracted with DCM (×3). The combined organic phases are successively washed with $H_2O$ and brine, dried over $Na_2SO_4$, filtered and concentrated under reduced pressure to afford the free primary amine, which is used in the next step without further purification.

With PG=Cbz:

A mixture of 2 mmol of the Cbz-protected amine, Pd—C 10% (100 mg) in dry EtOH (25 mL) is stirred at RT under hydrogen atmosphere for 3 h. The reaction mixture is filtered over Celite and concentrated under reduced pressure to afford the free primary amine, which is used in the next step without further purification.

Intermediates 2

General Methods C1 & C2—Step 3

Scheme 9

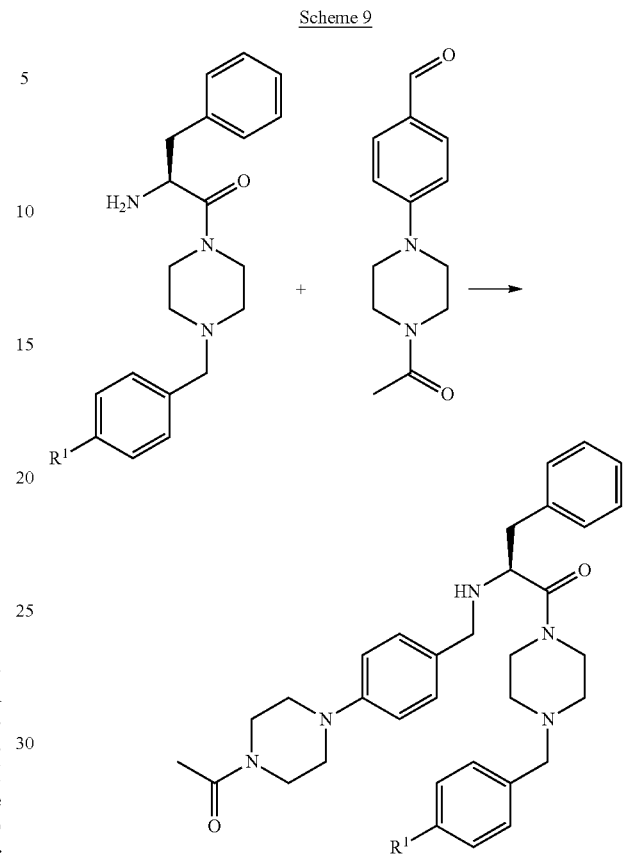

General Method C1:

A solution of 1 mmol of amine and 1 mmol of aldehyde in 5 mL of dry MeOH is refluxed for 24 h under nitrogen. The resulting mixture is then cooled to RT prior to the addition of 1.5 mmol of $NaBH_4$ in portion. The obtained heterogeneous mixture is further stirred for 2 h at RT, quenched with a saturated aqueous solution of $NaHCO_3$ and extracted with EtOAc (×3). The combined organic phases are washed with brine, dried over $Na_2SO_4$, filtered and concentrated under reduced pressure. The residue is purified by flash chromatography ($SiO_2$ 60F) to afford the title compound.

| | | | LC-MS | |
|---|---|---|---|---|
| $R^1$ | Chemical name | Yield | Rt (min) | $[M + H]^+$ |
| H | (S)-2-Amino-1-(4-benzyl-piperazin-1-yl)-3-phenyl-propan-1-one | Quant. | 0.79* | 324.29 |
| CN | (S)-4-[4-(2-Amino-3-phenyl-propionyl)-piperazin-1-ylmethyl]-benzonitrile | Quant. | 0.74* | 349.16 |
| $N(CH_3)_2$ | (S)-2-Amino-1-[4-(4-dimethylamino-benzyl)piperazin-1-yl]-3-phenyl-propan-1-one | Quant. | 0.78* | 367.19 |
| Cl | (S)-2-Amino-1-[4-(4-chloro-benzyl)-piperazin-1-yl]-3-phenyl-propan-1-one | Quant. | 0.82* | 358.11 |
| $S(O_2)Me$ | (S)-2-Amino-1-(4-(4-(methylsulfonyl)benzyl)piperazin-1-yl)-3-phenylpropan-1-one | 89% | 0.37** | 401.79 |
| $S(O_2)Et$ | (S)-2-Amino-1-(4-(4-(ethylsulfonyl)benzyl)piperazin-1-yl)-3-phenylpropan-1-one | 88% | 0.4** | 416.07 |

*Analytic I, X-Bridge column, basic conditions.
**Analytic, Waters Atlantis T3 column, acidic conditions General Method C2:

To a solution of 1 mmol of amine and 1 mmol of aldehyde in 5 mL of dry $CH_3CN$ are added portionwise 1.5 mmol of $NaBH(OAc)_3$. The resulting heterogeneous mixture is further stirred for 4 h at RT, quenched with a saturated aqueous solution of $NaHCO_3$ and extracted with EtOAc (×3). The combined organic phases are washed with brine, dried over $Na_2SO_4$, filtered and concentrated under reduced pressure. The residue is purified by flash chromatography ($SiO_2$ 60F) to afford the title compound.

Intermediates 3

| | | | LC-MS | |
| --- | --- | --- | --- | --- |
| $R^1$ | Chemical name | Yield | Rt (min) | $[M + H]^+$ |
| H | (S)-2-[4-(4-Acetyl-piperazin-1-yl)-benzylamino]-1-(4-benzyl-piperazin-1-yl)-3-phenyl-propan-1-one | 77% | 0.84* | 540.30 |
| CN | (S)-4-(4-{2-[4-(4-Acetyl-piperazin-1-yl)-benzylamino]-3-phenyl-propionyl}-piperazin-1-ylmethyl)-benzonitrile | 81% | 0.79* | 565.16 |
| $N(CH_3)_2$ | (S)-2-[4-(4-Acetyl-piperazin-1-yl)-benzylamino]-1-[4-(4-dimethylamino-benzyl)-piperazin-1-yl]-3-phenyl-propan-1-one | 64% | 0.83* | 583.20 |
| Cl | (S)-2-[4-(4-Acetyl-piperazin-1-yl)-benzylamino]-1-[4-(4-chloro-benzyl)-piperazin-1-yl]-3-phenyl-propan-1-one | 76% | 0.88* | 574.10 |
| $S(O_2)Me$ | (S)-2-[4-(4-Acetyl-piperazin-1-yl)-benzylamino]-1-[4-(4-methylsulfonyl-benzyl)-piperazin-1-yl]-3-phenyl-propan-1-one | 52% | 0.43** | 618.22 |
| $S(O_2)Et$ | (S)-2-[4-(4-Acetyl-piperazin-1-yl)-benzylamino]-1-[4-(4-ethylsulfonyl-benzyl)-piperazin-1-yl]-3-phenyl-propan-1-one | 80% | 0.45** | 632.2 |

*Analytic I, X-Bridge column, basic conditions.
**Analytic, Waters Atlantis T3 column, acidic conditions General Methods D1 and D2—Step 4

Scheme 10

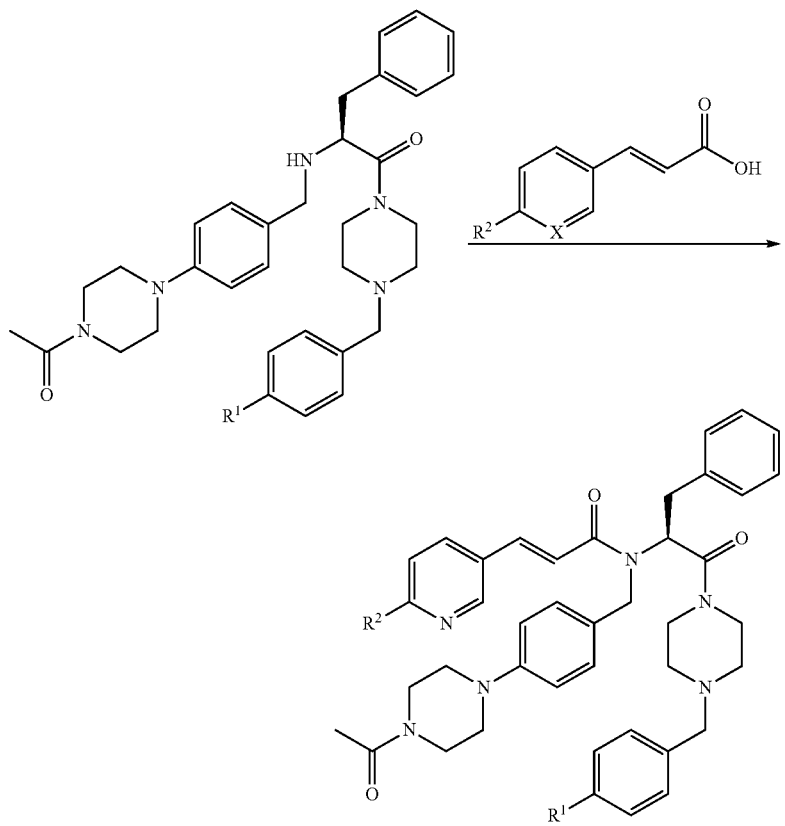

General Method D1:

To a solution of 1 mmol of cinnamic acid in 5 mL of dry DCM under nitrogen are added 1.4 mmol of 1-chloro-N,N-2-trimethylpropenylamine (Ghosez's reagent). The resulting mixture is stirred at RT for 1 h before a solution of 1 mmol of amine and 3 mmol of DIPEA in 4 mL of dry DCM is added. The reaction mixture is further stirred at RT overnight. Upon completion a saturated aqueous solution of NaHCO$_3$ is added and the mixture extracted with DCM (×3). The combined organic phases are washed with brine, dried over Na$_2$SO$_4$, filtered and concentrated under reduced pressure. The residue is purified either by flash chromatography (SiO$_2$ 60F) or by preparative HPLC to afford the final compound.

General Method D2:

To a solution (or suspension) of 1.05 mmol of cinnamic acid in 3.5 mL of dry DCM under nitrogen at 0° C. are added 1.1 mmol of oxalyl chloride and 3 drops of DMF. The resulting mixture is stirred at RT for 1 h, cooled down to 0° C. before a solution of 1 mmol of amine and 2 mmol of DIPEA in 3 mL of dry DCM is added. The reaction mixture is further stirred at RT overnight. Upon completion a saturated aqueous solution of NaHCO$_3$ is added and the mixture extracted with DCM (×3). The combined organic phases are washed with brine, dried over Na$_2$SO$_4$, filtered and concentrated under reduced pressure. The residue is purified either by flash chromatography (SiO$_2$ 60F) or by preparative HPLC to afford the final compound.

| Compound of Example # | Chemical name | LC-MS Rt (min) | [M + H]$^+$ |
|---|---|---|---|
| 1** | (S)-N-[4-(4-Acetyl-piperazin-1-yl)-benzyl]-N-[1-benzyl-2-(4-benzyl-piperazin-1-yl)-2-oxo-ethyl]-3-(4-trifluoromethyl-phenyl)-acrylamide | 1.00* | 738.37 |
| 2 | (S)-N-[4-(4-Acetyl-piperazin-1-yl)-benzyl]-N-[1-benzyl-2-(4-benzyl-piperazin-1-yl)-2-oxo-ethyl]-3-(4-ethyl-phenyl)-acrylamide | 1.02* | 698.45 |
| 3 | (S)-N-[4-(4-Acetyl-piperazin-1-yl)-benzyl]-N-[1-benzyl-2-(4-benzyl-piperazin-1-yl)-2-oxo-ethyl]-3-(4-tert-butyl-phenyl)-acrylamide | 1.06* | 726.46 |
| 4 | (S)-N-[4-(4-Acetyl-piperazin-1-yl)-benzyl]-N-[1-benzyl-2-(4-benzyl-piperazin-1-yl)-2-oxo-ethyl]-3-(4-ethoxy-phenyl)-acrylamide | 0.98* | 714.26 |
| 5 | (S)-4-(2-{[4-(4-Acetyl-piperazin-1-yl)-benzyl]-[1-benzyl-2-(4-benzyl-piperazin-1-yl)-2-oxo-ethyl]-carbamoyl}-vinyl)-benzoic acid methyl ester | 0.94* | 728.39 |
| 6 | (S)-N-[4-(4-Acetyl-piperazin-1-yl)-benzyl]-N-[1-benzyl-2-(4-benzyl-piperazin-1-yl)-2-oxo-ethyl]-3-(4-methanesulfonyl-phenyl)-acrylamide | 0.88* | 748.36 |
| 7 | (S)-3-(4-Acetylamino-phenyl)-N-[4-(4-acetyl-piperazin-1-yl)benzyl]-N-[1-benzyl-2-(4-benzyl-piperazin-1-yl)-2-oxo-ethyl]-acrylamide | 0.86* | 727.37 |
| 8 | (S)-N-[4-(4-Acetyl-piperazin-1-yl)-benzyl]-N-[1-benzyl-2-(4-benzyl-piperazin-1-yl)-2-oxo-ethyl]-3-(4-propoxy-phenyl)-acrylamide | 1.02* | 728.40 |
| 9 | (S)-N-[4-(4-Acetyl-piperazin-1-yl)-benzyl]-N-[1-benzyl-2-(4-benzyl-piperazin-1-yl)-2-oxo-ethyl]-3-(4-isopropoxy-phenyl)-acrylamide | 1.00* | 728.43 |
| 10 | (S)-N-[4-(4-Acetyl-piperazin-1-yl)-benzyl]-N-[1-benzyl-2-(4-benzyl-piperazin-1-yl)-2-oxo-ethyl]-3-(4-isopropyl-phenyl)-acrylamide | 1.05* | 712.28 |
| 11 | (S)-N-[4-(4-Acetyl-piperazin-1-yl)-benzyl]-N-{1-benzyl-2-[4-(4-dimethylamino-benzyl)-piperazin-1-yl]-2-oxo-ethyl}-3-(4-trifluoromethyl-phenyl)-acrylamide | 0.99* | 781.18 |
| 12 | (S)-N-[4-(4-Acetyl-piperazin-1-yl)-benzyl]-N-{1-benzyl-2-[4-(4-dimethylamino-benzyl)-piperazin-1-yl]-2-oxo-ethyl}-3-(6-trifluoromethyl-pyridin-3-yl)-acrylamide | 0.94* | 782.19 |
| 13 | (S)-N-[4-(4-Acetyl-piperazin-1-yl)-benzyl]-N-{1-benzyl-2-[4-(4-dimethylamino-benzyl)-piperazin-1-yl]-2-oxo-ethyl}-3-(6-methoxy-pyridin-3-yl)-acrylamide | 0.91* | 744.20 |
| 14 | (S)-N-[4-(4-Acetyl-piperazin-1-yl)-benzyl]-N-{1-benzyl-2-[4-(4-dimethylamino-benzyl)-piperazin-1-yl]-2-oxo-ethyl}-3-(6-ethoxy-pyridin-3-yl)-acrylamide | 0.94* | 758.22 |
| 15 | (S)-N-[4-(4-Acetyl-piperazin-1-yl)-benzyl]-N-{1-benzyl-2-[4-(4-dimethylamino-benzyl)-piperazin-1-yl]-2-oxo-ethyl}-3-(4-ethoxy-phenyl)-acrylamide | 0.97* | 757.17 |
| 16 | (S)-N-[4-(4-Acetyl-piperazin-1-yl)-benzyl]-N-{1-benzyl-2-[4-(4-dimethylamino-benzyl)-piperazin-1-yl]-2-oxo-ethyl}-3-(4-methanesulfonyl-phenyl)-acrylamide | 0.87* | 791.15 |
| 17 | (S)-3-(4-Acetylamino-phenyl)-N-[4-(4-acetyl-perazin-1-yl)-benzyl]-N-{1-benzyl-2-[4-(4-dimethylamino-benzyl)-piperazin-1-yl]-2-oxo-ethyl}-acrylamide | 0.85* | 770.22 |

-continued

| Compound of Example # | Chemical name | LC-MS Rt (min) | [M + H]+ |
|---|---|---|---|
| 18 | (S)-N-[4-(4-Acetyl-piperazin-1-yl)-benzyl]-N-{1-benzyl-2-[4-(4-dimethylamino-benzyl)-piperazin-1-yl]-2-oxo-ethyl}-3-(4-propoxy-phenyl)-acrylamide | 1.00* | 771.27 |
| 19 | (S)-N-[4-(4-Acetyl-piperazin-1-yl)-benzyl]-N-{1-benzyl-2-[4-(4-dimethylamino-benzyl)-piperazin-1-yl]-2-oxo-ethyl}-3-(4-isopropoxy-phenyl)-acrylamide | 0.99* | 771.25 |
| 20 | (S)-N-[4-(4-Acetyl-piperazin-1-yl)-benzyl]-N-{1-benzyl-2-[4-(4-dimethylamino-benzyl)-piperazin-1-yl]-2-oxo-ethyl}-3-(4-ethyl-phenyl)-acrylamide | 1.00* | 741.28 |
| 21 | (S)-N-[4-(4-Acetyl-piperazin-1-yl)-benzyl]-N-{1-benzyl-2-[4-(4-dimethylamino-benzyl)-piperazin-1-yl]-2-oxo-ethyl}-3-(4-difluoromethoxy-phenyl)-acrylamide | 0.95* | 779.15 |
| 22 | (S)-N-[4-(4-Acetyl-piperazin-1-yl)-benzyl]-N-{1-benzyl-2-[4-(4-dimethylamino-benzyl)-piperazin-1-yl]-2-oxo-ethyl}-3-(4-tert-butyl-phenyl)-acrylamide | 1.05* | 769.26 |
| 23 | (S)-N-[4-(4-Acetyl-piperazin-1-yl)-benzyl]-N-{1-benzyl-2-[4-(4-dimethylamino-benzyl)-piperazin-1-yl]-2-oxo-ethyl}-3-(4-isopropyl-phenyl)-acrylamide | 1.03* | 755.28 |
| 24 | (S)-N-[4-(4-Acetyl-piperazin-1-yl)-benzyl]-N-{1-benzyl-2-[4-(4-cyano-benzyl)-piperazin-1-yl]-2-oxo-ethyl}-3-(4-trifluoromethyl-phenyl)-acrylamide | 0.96* | 763.11 |
| 25 | (S)-N-[4-(4-Acetyl-piperazin-1-yl)-benzyl]-N-{1-benzyl-2-[4-(4-cyano-benzyl)-piperazin-1-yl]-2-oxo-ethyl}-3-(4-ethoxy-phenyl)-acrylamide | 0.93* | 739.22 |
| 26 | (S)-N-[4-(4-Acetyl-piperazin-1-yl)-benzyl]-N-{1-benzyl-2-[4-(4-cyano-benzyl)-piperazin-1-yl]-2-oxo-ethyl}-3-(4-methanesulfonyl-phenyl)-acrylamide | 0.84* | 773.00 |
| 27 | (S)-3-(4-Acetylamino-phenyl)-N-[4-(4-acetyl-piperazin-1-yl)-benzyl]-N-{1-benzyl-2-[4-(4-cyano-benzyl)piperazin-1-yl]-2-oxo-ethyl}-acrylamide | 0.82* | 752.02 |
| 28 | (S)-N-[4-(4-Acetyl-piperazin-1-yl)-benzyl]-N-{1-benzyl-2-[4-(4-cyano-benzyl)-piperazin-1-yl]-2-oxo-ethyl}-3-(4-propoxy-phenyl)-acrylamide | 0.97* | 753.15 |
| 29 | (S)-N-[4-(4-Acetyl-piperazin-1-yl)-benzyl]-N-{1-benzyl-2-[4-(4-cyano-benzyl)-piperazin-1-yl]-2-oxo-ethyl}-3-(4-isopropoxy-phenyl)-acrylamide | 0.96* | 753.18 |
| 30 | (S)-N-[4-(4-Acetyl-piperazin-1-yl)-benzyl]-N-{1-benzyl-2-[4-(4-cyano-benzyl)-piperazin-1-yl]-2-oxo-ethyl}-3-(4-ethyl-phenyl)-acrylamide | 0.97* | 723.19 |
| 31 | (S)-N-[4-(4-Acetyl-piperazin-1-yl)-benzyl]-N-{1-benzyl-2-[4-(4-cyano-benzyl)-piperazin-1-yl]-2-oxo-ethyl}-3-(4-difluoromethoxy-phenyl)-acrylamide | 0.92* | 761.06 |
| 32 | (S)-N-[4-(4-Acetyl-piperazin-1-yl)-benzyl]-N-{1-benzyl-2-[4-(4-cyano-benzyl)-piperazin-1-yl]-2-oxo-ethyl}-3-(4-isopropyl-phenyl)-acrylamide | 0.99* | 737.23 |
| 33 | (S)-N-[4-(4-Acetyl-piperazin-1-yl)-benzyl]-N-{1-benzyl-2-[4-(4-cyano-benzyl)-piperazin-1-yl]-2-oxo-ethyl}-3-(4-trifluoromethoxy-phenyl)-acrylamide | 0.97* | 778.97 |
| 34 | (S)-N-[4-(4-Acetyl-piperazin-1-yl)-benzyl]-N-{1-benzyl-2-[4-(4-cyano-benzyl)-piperazin-1-yl]-2-oxo-ethyl}-3-(4-tert-butyl-phenyl)-acrylamide | 1.02* | 751.21 |
| 35 | (S)-N-[4-(4-Acetyl-piperazin-1-yl)-benzyl]-N-{1-benzyl-2-[4-(4-chloro-benzyl)-piperazin-1-yl]-2-oxo-ethyl}-3-(4-ethoxy-phenyl)-acrylamide | 1.00* | 748.13 |
| 36 | (S)-N-[4-(4-Acetyl-piperazin-1-yl)-benzyl]-N-{1-benzyl-2-[4-(4-chloro-benzyl)-piperazin-1-yl]-2-oxo-ethyl}-3-(4-methanesulfonyl-phenyl)-acrylamide | 0.90* | 782.11 |
| 37 | (S)-3-(4-Acetylamino-phenyl)-N-[4-(4-acetyl-piperazin-1-yl)-benzyl]-N-{1-benzyl-2-[4-(4-chloro-benzyl)-piperazin-1-yl]-2-oxo-ethyl}-acrylamide | 0.88* | 761.18 |
| 38 | (S)-N-[4-(4-Acetyl-piperazin-1-yl)-benzyl]-N-{1-benzyl-2-[4-(4-chloro-benzyl)-piperazin-1-yl]-2-oxo-ethyl}-3-(4-propoxy-phenyl)-acrylamide | 1.03* | 762.18 |
| 39 | (S)-N-[4-(4-Acetyl-piperazin-1-yl)-benzyl]-N-{1-benzyl-2-[4-(4-chloro-benzyl)-piperazin-1-yl]-2-oxo-ethyl}-3-(4-isopropoxy-phenyl)-acrylamide | 1.02* | 762.13 |
| 40 | (S)-N-[4-(4-Acetyl-piperazin-1-yl)-benzyl]-N-{1-benzyl-2-[4-(4-chloro-benzyl)-piperazin-1-yl]-2-oxo-ethyl}-3-(4-ethyl-phenyl)-acrylamide | 1.04* | 732.25 |
| 41 | (S)-N-[4-(4-Acetyl-piperazin-1-yl)-benzyl]-N-{1-benzyl-2-[4-(4-chloro-benzyl)-piperazin-1-yl]-2-oxo-ethyl}-3-(4-difluoromethoxy-phenyl)-acrylamide | 0.98* | 770.15 |

-continued

| Compound of Example # | Chemical name | LC-MS Rt (min) | [M + H]+ |
|---|---|---|---|
| 42 | (S)-N-[4-(4-Acetyl-piperazin-1-yl)-benzyl]-N-{1-benzyl-2-[4-(4-chloro-benzyl)-piperazin-1-yl]-2-oxo-ethyl}-3-(4-isopropyl-phenyl)-acrylamide | 1.06* | 745.96 |
| 43 | (S)-N-[4-(4-Acetyl-piperazin-1-yl)-benzyl]-N-{1-benzyl-2-[4-(4-chloro-benzyl)-piperazin-1-yl]-2-oxo-ethyl}-3-(4-tert-butyl-phenyl)-acrylamide | 1.08* | 760.13 |
| 44 | (S)-N-[4-(4-Acetyl-piperazin-1-yl)-benzyl]-N-{1-benzyl-2-[4-(4-(methylsulfonyl)-benzyl)-piperazin-1-yl]-2-oxo-ethyl}-3-(4-isopropoxyphenyl)-acrylamide | 0.73*** | 806.37 |
| 45 | (S)-N-[4-(4-Acetyl-piperazin-1-yl)-benzyl]-N-{1-benzyl-2-[4-(4-(methylsulfonyl)-benzyl)-piperazin-1-yl]-2-oxo-ethyl}-3-(4-tert-butyl-phenyl)-acrylamide | 0.78*** | 804.37 |
| 46 | (S)-N-[4-(4-Acetyl-piperazin-1-yl)-benzyl]-N-{1-benzyl-2-[4-(4-(methylsulfonyl)-benzyl)-piperazin-1-yl]-2-oxo-ethyl}-3-(4-propoxyphenyl)-acrylamide | 0.76*** | 806.37 |
| 47 | (S)-N-(4-(4-acetylpiperazin-1-yl)benzyl)-N-(1-(4-(4-(methylsulfonyl)benzyl)piperazin-1-yl)-1-oxo-3-phenylpropan-2-yl)-3-(4-(trifluoromethyl)phenyl)acrylamide | 0.75*** | 816.23 |
| 48 | (S)-N-[4-(4-Acetyl-piperazin-1-yl)-benzyl]-N-{1-benzyl-2-[4-(4-(ethylsulfonyl)-benzyl)-piperazin-1-yl]-2-oxo-ethyl}-3-(4-propoxyphenyl)-acrylamide | 0.77*** | 820.43 |
| 49 | (S)-N-(4-(4-acetylpiperazin-1-yl)benzyl)-N-(1-(4-(4-(ethylsulfonyl)benzyl)piperazin-1-yl)-1-oxo-3-phenylpropan-2-yl)-3-(4-(trifluoromethyl)phenyl)acrylamide | 0.76*** | 829.85 |

*Analytic I, X-Bridge column, basic conditions.
**Reference Example
***Analytic, Waters Atlantis T3 column, acidic conditions Preparation of Compounds of Formula I Via Pathway Depicted in Scheme 2

General Procedures and Examples

Step 1: (S)-[1-Benzyl-2-(4-{4-[(2-hydroxy-ethyl)-methyl-amino]-benzyl}-piperazin-1-yl)-2-oxo-ethyl]-carbamic acid tert-butyl ester Scheme 11

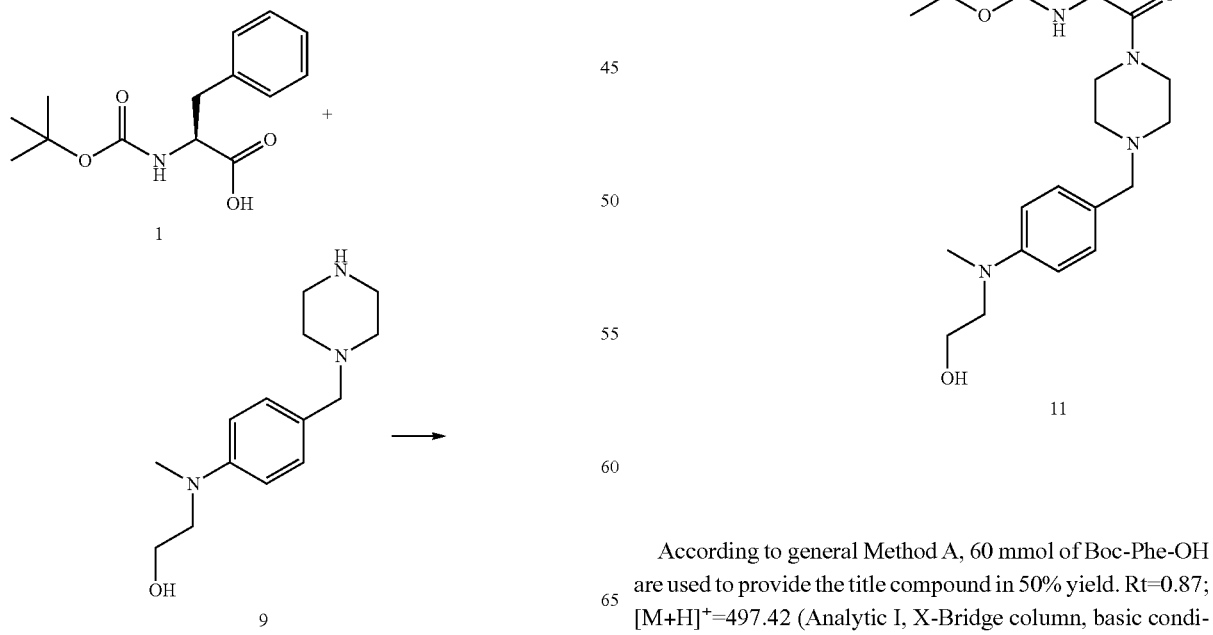

According to general Method A, 60 mmol of Boc-Phe-OH are used to provide the title compound in 50% yield. Rt=0.87; [M+H]+=497.42 (Analytic I, X-Bridge column, basic conditions).

Step 2: (S)-2-Amino-1-(4-{4-[(2-hydroxy-ethyl)-methyl-amino]-benzyl}-piperazin-1-yl)-3-phenyl-propan-1-one Scheme 12

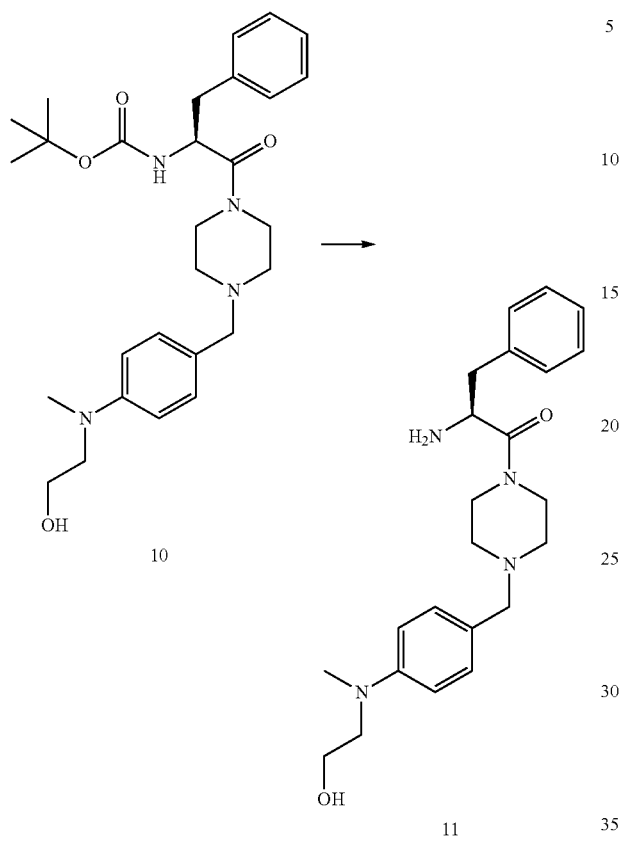

According to general Method B, 12 mmol of Boc-protected amine 10 are used to provide the title compound in quantitative yield. Rt=0.69; [M+H]⁺=397.18 (Analytic I, X-Bridge column, basic conditions).

Step 3: (S)-2-[4-(4-Acetyl-piperazin-1-yl)-benzylamino]-1-(4-{4-[(2-hydroxy-ethyl)-methyl-amino]-benzyl}-piperazin-1-yl)-3-phenyl-propan-1-one Scheme 13

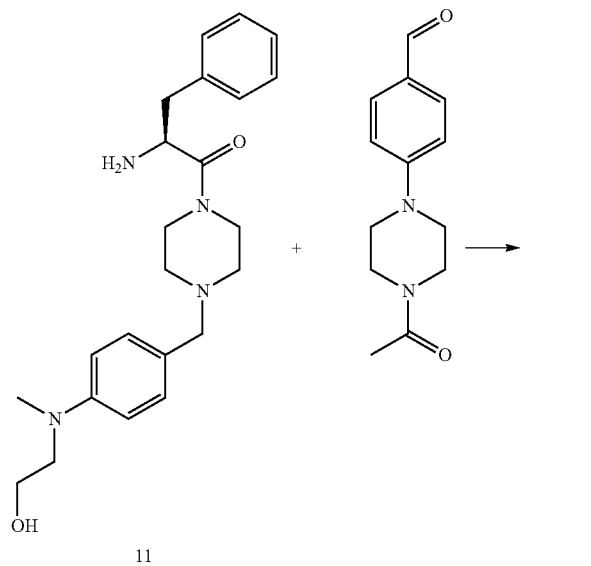

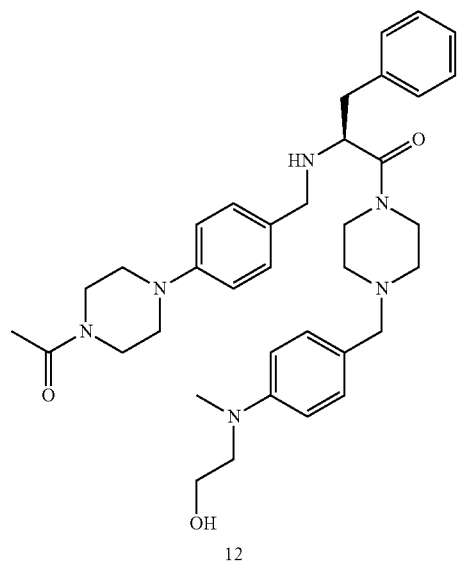

According to general Method C2, 11.4 mmol of free amine 11 are used to provide the title compound in quantitative yield. Rt=0.74; [M+H]⁺=613.24 (Analytic I, X-Bridge column, basic conditions).

General Method E—Step 4: (S)-2-[4-(4-Acetyl-piperazin-1-yl)-benzylamino]-1-[4-(4-{[2-(tert-butyl-dimethyl-silanyloxy)-ethyl]-methyl-amino}-benzyl)-piperazin-1-yl]-3-phenyl-propan-1-one Scheme 14

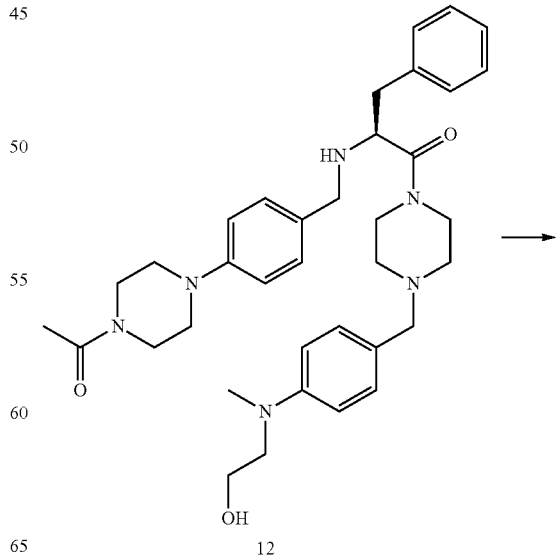

-continued

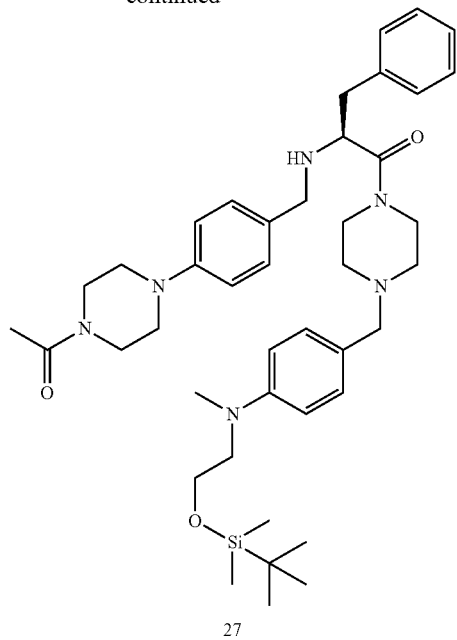

27

3 mmol of TBDMSCl are added portionwise to a solution of 1 mmol of hydroxyl 12 and 3 mmol of imidazole in 5 mL of dry DMF at RT. The yellow solution is stirred at RT for 16 h, quenched with $H_2O$ and extracted with EtOAc (×3). The combined organic phases are washed with brine, dried over $Na_2SO_4$, filtered and concentrated under reduced pressure. The residue is purified by flash chromatography ($SiO_2$ 60F; DCM/MeOH 92:8 to 95:5) to afford the title compound as yellow foam in 81% yield. Rt=1.12 min; $[M+H]^+$=727.31. (Analytic I, X-Bridge column, basic conditions).

Step 5

Scheme 15

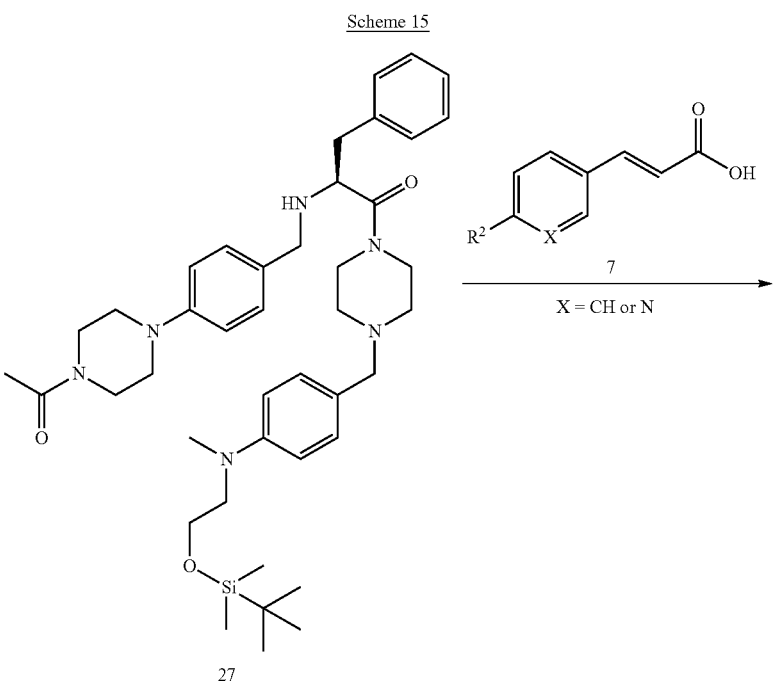

27

-continued

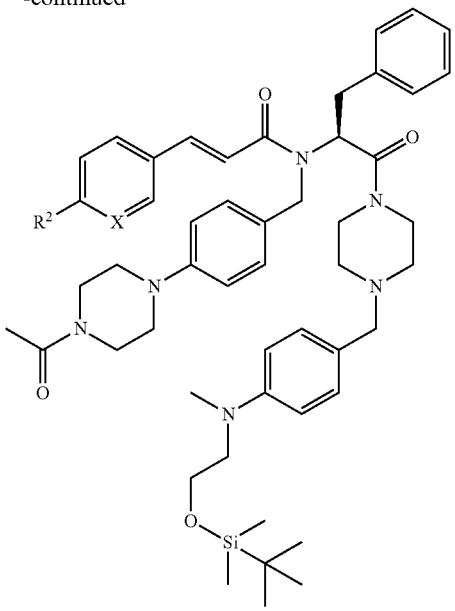

28

The compounds of formula 28 are obtained according to general Methods D1 or D2.

| Intermediate # | Chemical name | LC-MS* Rt (min) | [M + H]+ |
|---|---|---|---|
| 4 | (S)-N-[4-(4-Acetyl-piperazin-1-yl)-benzyl]-N-{1-benzyl-2-[4-(4-{[2-(tert-butyl-dimethyl-silanyloxy)-ethyl]-methyl-amino}-benzyl)-piperazin-1-yl]-2-oxo-ethyl}-3-(4-trifluoromethyl-phenyl)-acrylamide | 1.21 | 925.21 |
| 5 | (S)-N-[4-(4-Acetyl-piperazin-1-yl)-benzyl]-N-{1-benzyl-2-[4-(4-{[2-(tert-butyl-dimethyl-silanyloxy)-ethyl]-methyl-amino}-benzyl)-piperazin-1-yl]-2-oxo-ethyl}-3-(6-trifluoromethyl-pyridin-3-yl)-acrylamide | 1.15 | 926.27 |
| 6 | (S)-N-[4-(4-Acetyl-piperazin-1-yl)-benzyl]-N-{1-benzyl-2-[4-(4-{[2-(tert-butyl-dimethyl-silanyloxy)-ethyl]-methyl-amino}-benzyl)-piperazin-1-yl]-2-oxo-ethyl}-3-(6-methoxy-pyridin-3-yl)-acrylamide | 1.14 | 888.29 |
| 7 | (S)-N-[4-(4-Acetyl-piperazin-1-yl)-benzyl]-N-{1-benzyl-2-[4-(4-{[2-(tert-butyl-dimethyl-silanyloxy)-ethyl]-methyl-amino}-benzyl)-piperazin-1-yl]-2-oxo-ethyl}-3-(6-ethoxy-pyridin-3-yl)-acrylamide | 1.19 | 902.33 |
| 8 | (S)-N-[4-(4-Acetyl-piperazin-1-yl)-benzyl]-N-{1-benzyl-2-[4-(4-{[2-(tert-butyl-dimethyl-silanyloxy)-ethyl]-methyl-amino}-benzyl)-piperazin-1-yl]-2-oxo-ethyl}-3-(4-ethoxy-phenyl)-acrylamide | 1.20 | 901.29 |
| 9 | (S)-N-[4-(4-Acetyl-piperazin-1-yl)-benzyl]-N-{1-benzyl-2-[4-(4-{[2-(tert-butyl-dimethyl-silanyloxy)-ethyl]-methyl-amino}-benzyl)-piperazin-1-yl]-2-oxo-ethyl}-3-(4-methanesulfonyl-phenyl)-acrylamide | 1.09 | 935.21 |
| 10 | (S)-3-(4-Acetylamino-phenyl)-N-[4-(4-acetyl-piperazin-1-yl)-benzyl]-N-{1-benzyl-2-[4-(4-{[2-(tert-butyl-dimethyl-silanyloxy)-ethyl]-methyl-amino}-benzyl)-piperazin-1-yl]-2-oxo-ethyl}-acrylamide | 1.08 | 914.29 |
| 11 | (S)-N-[4-(4-Acetyl-piperazin-1-yl)-benzyl]-N-{1-benzyl-2-[4-(4-{[2-(tert-butyl-dimethyl-silanyloxy)-ethyl]-methyl-amino}-benzyl)-piperazin-1-yl]-2-oxo-ethyl}-3-(4-propoxy-phenyl)-acrylamide | 1.24 | 915.28 |

-continued

| Intermediate # | Chemical name | LC-MS* Rt (min) | [M + H]+ |
|---|---|---|---|
| 12 | (S)-N-[4-(4-Acetyl-piperazin-1-yl)-benzyl]-N-{1-benzyl-2-[4-(4-{[2-(tert-butyl-dimethyl-silanyloxy)-ethyl]-methyl-amino}-benzyl)-piperazin-1-yl]-2-oxo-ethyl}-3-(4-isopropoxy-phenyl)-acrylamide | 1.22 | 915.32 |
| 13 | (S)-N-[4-(4-Acetyl-piperazin-1-yl)-benzyl]-N-{1-benzyl-2-[4-(4-{[2-(tert-butyl-dimethyl-silanyloxy)-ethyl]-methyl-amino}-benzyl)-piperazin-1-yl]-2-oxo-ethyl}-3-(4-ethyl-phenyl)-acrylamide | 1.25 | 885.35 |
| 14 | (S)-N-[4-(4-Acetyl-piperazin-1-yl)-benzyl]-N-{1-benzyl-2-[4-(4-{[2-(tert-butyl-dimethyl-silanyloxy)-ethyl]-methyl-amino}-benzyl)-piperazin-1-yl]-2-oxo-ethyl}-3-(4-difluoromethoxy-phenyl)-acrylamide | 1.15 | 923.21 |
| 15 | (S)-N-[4-(4-Acetyl-piperazin-1-yl)-benzyl]-N-{1-benzyl-2-[4-(4-{[2-(tert-butyl-dimethyl-silanyloxy)-ethyl]-methyl-amino}-benzyl)-piperazin-1-yl]-2-oxo-ethyl}-3-(4-isopropyl-phenyl)-acrylamide | 1.29 | 899.32 |
| 16 | (S)-N-[4-(4-Acetyl-piperazin-1-yl)-benzyl]-N-{1-benzyl-2-[4-(4-{[2-(tert-butyl-dimethyl-silanyloxy)-ethyl]-methyl-amino}-benzyl)-piperazin-1-yl]-2-oxo-ethyl}-3-(4-tert-butyl-phenyl)-acrylamide | 1.32 | 913.29 |

*Analytic I, X-Bridge column, basic conditions.

General Method F—Step 6

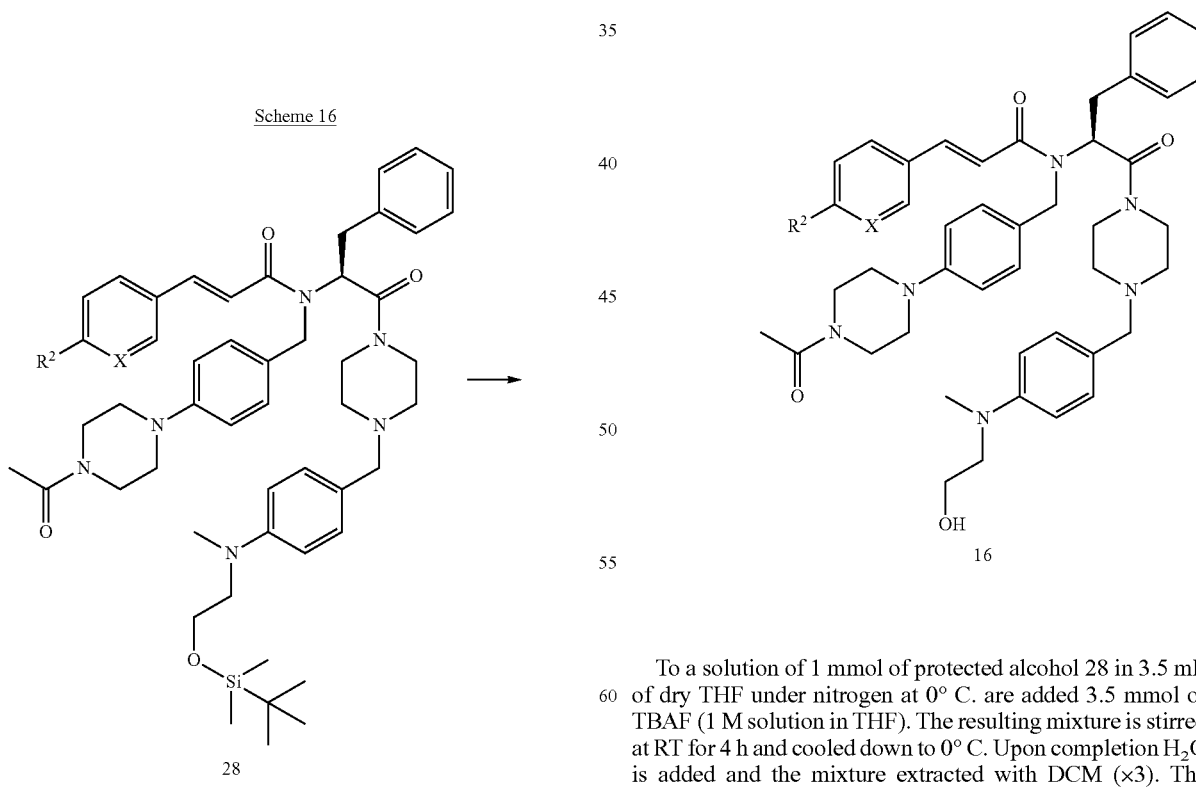

To a solution of 1 mmol of protected alcohol 28 in 3.5 mL of dry THF under nitrogen at 0° C. are added 3.5 mmol of TBAF (1 M solution in THF). The resulting mixture is stirred at RT for 4 h and cooled down to 0° C. Upon completion H$_2$O is added and the mixture extracted with DCM (×3). The combined organic phases are washed with brine, dried over Na$_2$SO$_4$, filtered and concentrated under reduced pressure. The residue is purified either by flash chromatography (SiO$_2$ 60F) or by preparative HPLC to afford the final compound.

| Compound of | | LC-MS* | |
|---|---|---|---|
| Example # | Chemical name | Rt (min) | [M + H]+ |
| 50 | (S)-N-[4-(4-Acetyl-piperazin-1-yl)-benzyl]-N-[1-benzyl-2-(4-{4-[(2-hydroxy-ethyl)-methyl-amino]-benzyl}-piperazin-1-yl)-2-oxo-ethyl]-3-(4-trifluoromethyl-phenyl)-acrylamide | 0.91 | 811.21 |
| 51 | (S)-N-[4-(4-Acetyl-piperazin-1-yl)-benzyl]-N-[1-benzyl-2-(4-{4-[(2-hydroxy-ethyl)-methyl-amino]-benzyl}-piperazin-1-yl)-2-oxo-ethyl]-3-(6-trifluoromethyl-pyridin-3-yl)-acrylamide | 0.86 | 812.24 |
| 52 | (S)-N-[4-(4-Acetyl-piperazin-1-yl)-benzyl]-N-[1-benzyl-2-(4-{4-[(2-hydroxy-ethyl)-methyl-amino]-benzyl}-piperazin-1-yl)-2-oxo-ethyl]-3-(6-methoxy-pyridin-3-yl)-acrylamide | 0.82 | 774.25 |
| 53 | (S)-N-[4-(4-Acetyl-piperazin-1-yl)-benzyl]-N-[1-benzyl-2-(4-{4-[(2-hydroxy-ethyl)-methyl-amino]-benzyl}-piperazin-1-yl)-2-oxo-ethyl]-3-(6-ethoxy-pyridin-3-yl)-acrylamide | 0.85 | 788.24 |
| 54 | (S)-N-[4-(4-Acetyl-piperazin-1-yl)-benzyl]-N-[1-benzyl-2-(4-{4-[(2-hydroxy-ethyl)-methyl-amino]-benzyl}-piperazin-1-yl)-2-oxo-ethyl]-3-(4-ethoxy-phenyl)-acrylamide | 0.88 | 787.19 |
| 55 | (S)-N-[4-(4-Acetyl-piperazin-1-yl)-benzyl]-N-[1-benzyl-2-(4-{4-[(2-hydroxy-ethyl)-methyl-amino]-benzyl}-piperazin-1-yl)-2-oxo-ethyl]-3-(4-methanesulfonyl-phenyl)-acrylamide | 0.80 | 821.18 |
| 56 | (S)-3-(4-Acetylamino-phenyl)-N-[4-(4-acetyl-piperazin-1-yl)-benzyl]-N-[1-benzyl-2-(4-{4-[(2-hydroxy-ethyl)-methyl-amino]-benzyl}-piperazin-1-yl)-2-oxo-ethyl]-acrylamide | 0.77 | 800.21 |
| 57 | (S)-N-[4-(4-Acetyl-piperazin-1-yl)-benzyl]-N-[1-benzyl-2-(4-{4-[(2-hydroxy-ethyl)-methyl-amino]-benzyl}-piperazin-1-yl)-2-oxo-ethyl]-3-(4-propoxy-phenyl)-acrylamide | 0.92 | 801.22 |
| 58 | (S)-N-[4-(4-Acetyl-piperazin-1-yl)-benzyl]-N-[1-benzyl-2-(4-{4-[(2-hydroxy-ethyl)-methyl-amino]-benzyl}-piperazin-1-yl)-2-oxo-ethyl]-3-(4-isopropoxy-phenyl)-acrylamide | 0.91 | 801.25 |
| 59 | (S)-N-[4-(4-Acetyl-piperazin-1-yl)-benzyl]-N-[1-benzyl-2-(4-{4-[(2-hydroxy-ethyl)-methyl-amino]-benzyl}-piperazin-1-yl)-2-oxo-ethyl]-3-(4-ethyl-phenyl)-acrylamide | 0.92 | 771.29 |
| 60 | (S)-N-[4-(4-Acetyl-piperazin-1-yl)-benzyl]-N-[1-benzyl-2-(4-{4-[(2-hydroxy-ethyl)-methyl-amino]-benzyl}-piperazin-1-yl)-2-oxo-ethyl]-3-(4-difluoromethoxy-phenyl)-acrylamide | 0.87 | 808.87 |
| 61 | (S)-N-[4-(4-Acetyl-piperazin-1-yl)-benzyl]-N-[1-benzyl-2-(4-{4-[(2-hydroxy-ethyl)-methyl-amino]-benzyl}-piperazin-1-yl)-2-oxo-ethyl]-3-(4-isopropyl-phenyl)-acrylamide | 0.94 | 787.34 |
| 62 | (S)-N-[4-(4-Acetyl-piperazin-1-yl)-benzyl]-N-[1-benzyl-2-(4-{4-[(2-hydroxy-ethyl)-methyl-amino]-benzyl}-piperazin-1-yl)-2-oxo-ethyl]-3-(4-tert-butyl-phenyl)-acrylamide | 0.97 | 799.22 |

*Analytic I, X-Bridge column, basic conditions.

Preparation of Compounds of Formula I Via Pathway Depicted in Scheme 3

General Procedures and Examples

Step 1: (S)-2-[4-(4-Acetyl-piperazin-1-yl)-benzylamino]-3-phenyl-propionic acid methyl ester Scheme 17
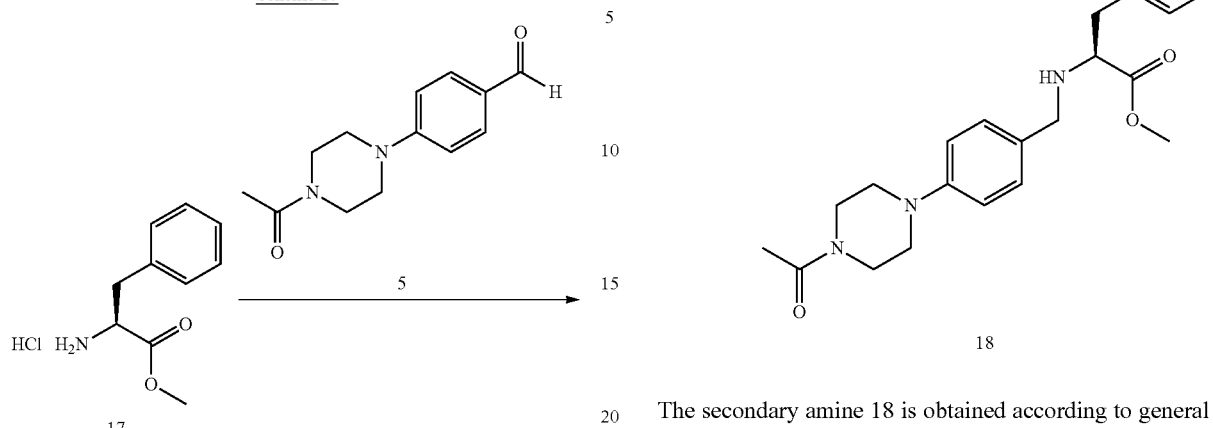
The secondary amine 18 is obtained according to general Methods C1 or C2 and used in the next step without further purification. Rt=0.82; [M+H]⁺=396.20 (Analytic I, X-Bridge column, basic conditions).
Step 2
Scheme 18
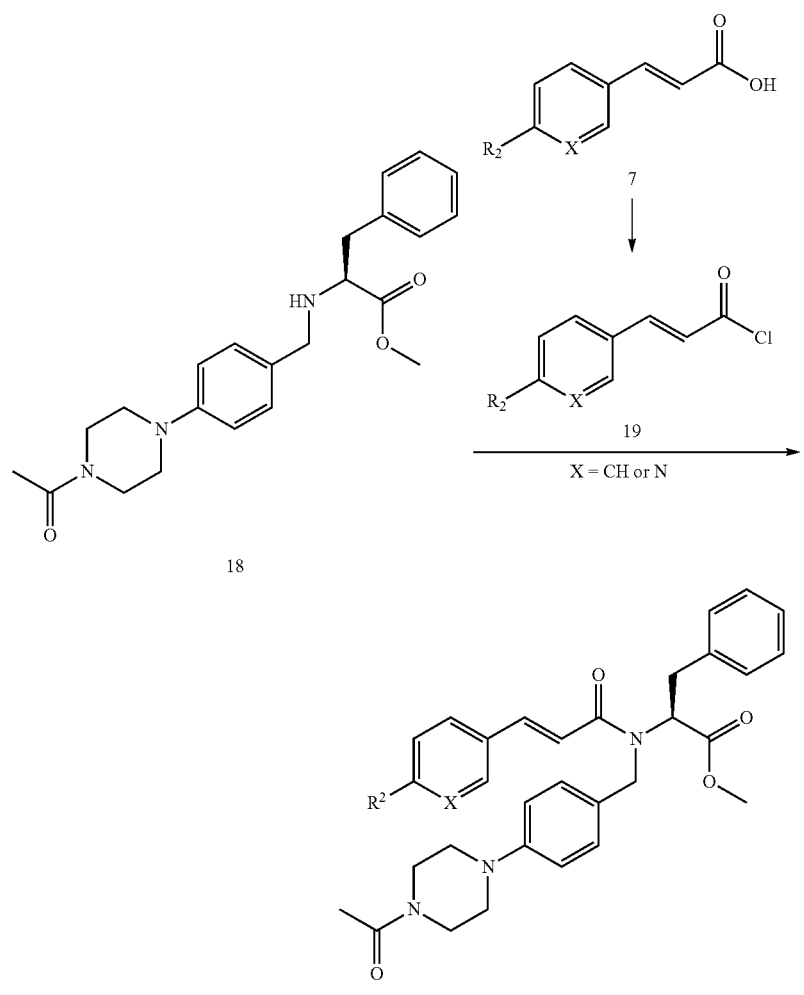

The compounds of formula 20 are obtained according to general Methods D1 or D2.

| Intermediate # | Chemical name | Yield | $t_R$ (min) | $[M + H]^+$ | LC-MS conditions |
|---|---|---|---|---|---|
| 17 | (S)-2-{[4-(4-Acetyl-piperazin-1-yl)-benzyl]-[3-(4-trifluoromethyl-phenyl)-acryloyl]-amino}-3-phenyl-propionic acid methyl ester | 70% | 0.96 | 594.15 | Analytic I, X-Bridge column, basic conditions | to pH=2-3 with HCl 1N and then extracted with EtOAc (×3). The combined organic phases are washed with brine, dried over $Na_2SO_4$, filtered and concentrated under reduced pressure. The residue is used in the next step without further purification.

| Intermediate # | Chemical name | Yield | $t_R$ (min) | $[M + H]^+$ | LC-MS conditions |
|---|---|---|---|---|---|
| 18 | (S)-2-{[4-(4-Acetyl-piperazin-1-yl)-benzyl]-[3-(4-trifluoromethyl-phenyl)-acryloyl]-amino}-3-phenyl-propionic acid | 78% | 0.97 | 580.12 | Analytic I, X-Bridge column, basic conditions |

General Method G—Step 3

Step 4

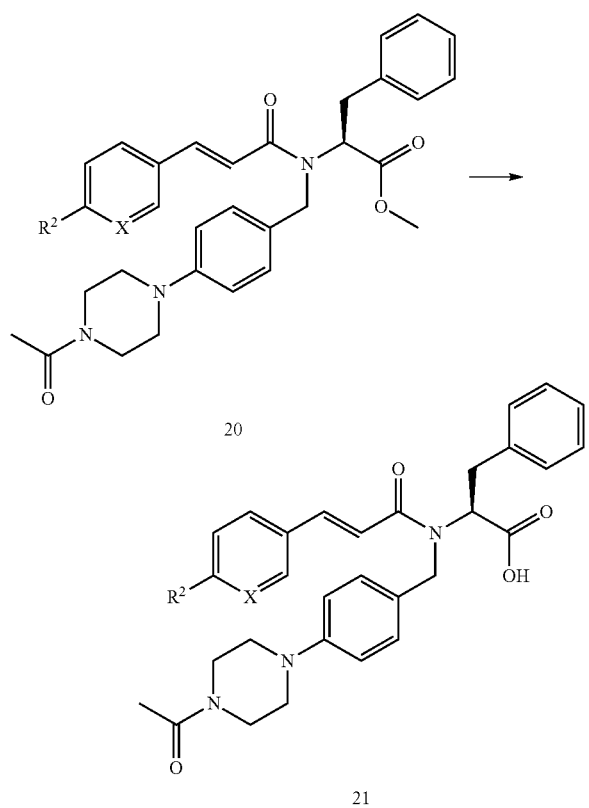

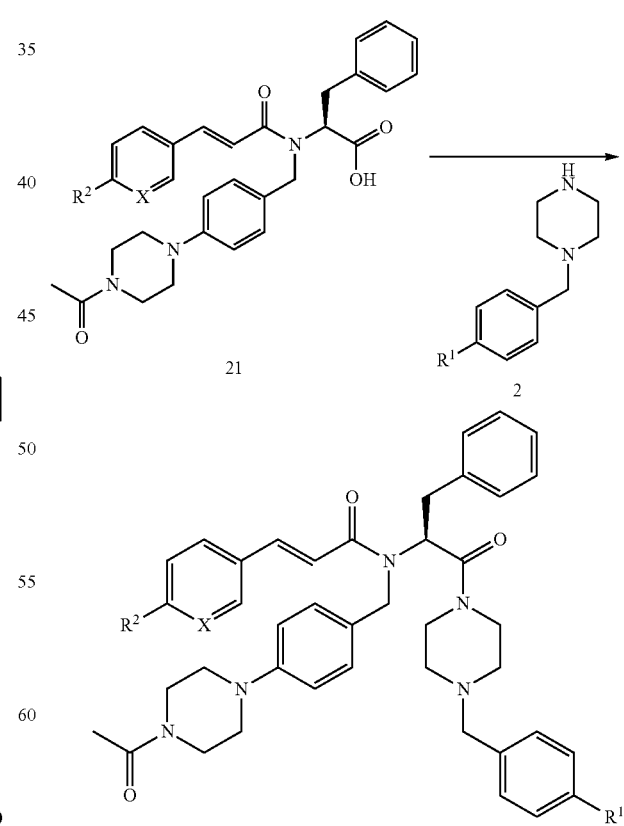

To a solution of 1 mmol of methyl ester 20 in 8 mL of $Et_2O$ and 2 mL of $H_2O$ at 0° C. are added dropwise 10 mmol of a 2M aqueous NaOH. The reaction mixture is further stirred at RT for 2-3 h. Upon completion the aqueous phase is acidified The compounds of formula 8 are obtained according to general Method A. The residue is purified either by flash chromatography ($SiO_2$ 60F) or by preparative HPLC to afford the final compound.

| Compound of | | LC-MS* | |
|---|---|---|---|
| Example # | Chemical name | Rt (min) | [M + H]+ |
| 63 | (S)-N-[4-(4-Acetyl-piperazin-1-yl)-benzyl]-N-{1-benzyl-2-[4-(4-methoxy-benzyl)-piperazin-1-yl]-2-oxo-ethyl}-3-(4-trifluoromethyl-phenyl)-acrylamide | 0.99 | 768.24 |
| 64 | (S)-N-[4-(4-Acetyl-piperazin-1-yl)-benzyl]-N-{1-benzyl-2-[4-(4-nitro-benzyl)-piperazin-1-yl]-2-oxo-ethyl}-3-(4-trifluoromethyl-phenyl)-acrylamide | 0.99 | 783.22 |
| 65 | (S)-N-[4-(4-Acetyl-piperazin-1-yl)-benzyl]-N-{1-benzyl-2-[4-(4-isopropoxy-benzyl)-piperazin-1-yl]-2-oxo-ethyl}-3-(4-trifluoromethyl-phenyl)-acrylamide | 1.02 | 796.24 |

*Analytic I, X-Bridge column, basic conditions.

The compounds of Examples 66 to 73 are obtained according to general Method D2.

| Compound of | | LC-MS* | |
|---|---|---|---|
| Example # | Chemical name | Rt (min) | [M + H]+ |
| 66 | (S)-N-[4-(4-Acetyl-piperazin-1-yl)benzyl]-N-{1-(4-(4-(dimethylamino)benzyl)piperazin-1-yl)-1-oxo-3-phenylpropan-2-yl}cinnamamide | 0.94 | 713.13 |
| 67 | (S)-N-[4-(4-Acetyl-piperazin-1-yl)benzyl]-N-{1-[4-(4-(dimethylamino)benzyl)piperazin-1-yl]-1-oxo-3-phenylpropan-2-yl}-3-(p-tolyl)acrylamide | 0.97 | 727.45 |
| 68 | (S)-N-[4-(4-Acetyl-piperazin-1-yl)benzyl]-N-{1-(4-(4-(dimethylamino)benzyl)piperazin-1-yl)-1-oxo-3-phenylpropan-2-yl}-3-(4-propylphenyl)acrylamide | 1.04 | 755.45 |
| 69 | (S)-N-[4-(4-Acetyl-piperazin-1-yl)benzyl]-N-{1-(4-(4-(dimethylamino)benzyl)piperazin-1-yl)-1-oxo-3-phenylpropan-2-yl}-3-(4-methoxyphenyl)acrylamide | 0.93 | 743.46 |
| 70 | (S)-3-(4-Acetyl-phenyl)-N-[4-(4-acetyl-piperazin-1-yl)benzyl]-N-{1-(4-(4-(dimethylamino)benzyl)piperazin-1-yl)-1-oxo-3-phenylpropan-2-yl}acrylamide | 0.91 | 755.43 |
| 71 | (S)-N-[4-(4-Acetyl-piperazin-1-yl)benzyl]-3-(4-cyanophenyl)-N-{1-(4-(4-(dimethylamino)benzyl)piperazin-1-yl)-1-oxo-3-phenylpropan-2-yl}acrylamide | 0.92 | 738.44 |
| 72 | (S)-N-[4-(4-Acetyl-piperazin-1-yl)benzyl]-N-{1-(4-(4-(dimethylamino)benzyl)piperazin-1-yl)-1-oxo-3-phenylpropan-2-yl}-3-(4-fluorophenyl)acrylamide | 0.95 | 731.42 |
| 73 | (S)-N-[4-(4-Acetyl-piperazin-1-yl)benzyl]-3-(4-chlorophenyl)-N-{1-(4-(4-(dimethylamino)benzyl)piperazin-1-yl)-1-oxo-3-phenylpropan-2-yl}acrylamide | 0.98 | 747.28 |

*Analytic I, X-Bridge column, basic conditions.

In Vitro Antimalarial Activity: *Plasmodium falciparum* In Vitro Assay

In vitro activity against erythrocytic stages of *P. falciparum* in human red blood cells is determined using a [$^3$H] hypoxanthine incorporation assay. One strain sensitive to all known drugs (*P. falciparum* NF54) is used in this assay and all tested compounds are compared for activity with the standard drugs chloroquine (sigma C6628) and artesunate (sigma 36, 159-3). Compounds, tested in duplicates, are serially diluted with screening medium [RPMI 1640 medium, supplemented with HEPES (5.94 g/L), $NaHCO_3$ (2.1 g/L), neomycin (100 U/mL), and Albumax (5 g/L) or human serum (50% final concentration)] in 96-well microtiter plates within an appropriate concentration range. Thereafter, the parasite cultures incubated in screening medium containing washed human red blood cells at 2.5% hematocrit (0.3% parasitemia) are added to the serially diluted compounds and incubated in a humidifying atmosphere at 37° C., 4% $CO_2$, 3% $O_2$, and 93% $N_2$. After 48 h, [$^3$H] hypoxanthine (0.5 µCi) is added to each well of a plate. The plates are incubated for a further 24 h under the same conditions then harvested with a Betaplate cell harvester (Wallac) and washed with distilled water. The dried filters are inserted into a plastic foil with 10 mL of scintillation fluid, and counted in a Betaplate liquid scintillation counter. $IC_{50}$ values are calculated from sigmoidal inhibition curves using Microsoft Excel.

TABLE 1

IC$_{50}$ values (nM) for compounds of formula I:

| Compound of Example # | IC$_{50}$ on NF54 (with Albumax) | IC$_{50}$ on NF54 (with 50% Serum) |
|---|---|---|
| 1 (Reference Example) | 5.1 | 27.6 |
| 2 | 2.0 | 10 |
| 3 | 1.9 | 8.5 |
| 4 | 1.9 | 10 |
| 5 | 3.9 | 12 |
| 6 | 9.4 | 32 |
| 7 | 3.1 | 40 |
| 8 | 1.8 | 13.4 |
| 9 | 2.4 | 7.3 |
| 10 | 3.0 | 8.6 |
| 11 | 4.0 | 21 |
| 12 | 17 | 74 |
| 13 | 12 | 46 |
| 14 | 3.7 | 20 |
| 15 | 1.7 | 6.8 |
| 16 | 5.5 | 13.3 |
| 17 | 4.3 | 39 |
| 18 | 2.5 | 11.8 |
| 19 | 2.6 | 9.3 |
| 20 | 1.2 | 7.1 |
| 21 | 1.9 | 7 |
| 22 | 1.3 | 10.9 |
| 23 | 1.3 | 9.5 |
| 24 | 2.8 | 13.9 |
| 25 | 1.2 | 4.7 |
| 26 | 18 | 33 |
| 27 | 1.8 | 12.9 |
| 28 | 1.1 | 3.6 |
| 29 | 1.1 | 3.7 |
| 30 | 0.9 | 5.0 |
| 31 | 1.7 | 3.8 |
| 32 | 0.5 | 4.4 |
| 33 | 3.3 | 10.9 |
| 34 | 0.5 | 3.8 |
| 35 | 2.9 | 9 |
| 36 | 7.8 | 28 |
| 37 | 3.2 | 28 |
| 38 | 1.8 | 9 |
| 39 | 2.3 | 11 |
| 40 | 1.7 | 10.5 |
| 41 | 2.9 | 12.5 |
| 42 | 1.7 | 13.7 |
| 43 | 1.1 | 13.5 |
| 44 | 0.4 | 2.8 |
| 45 | 0.2 | 1.8 |
| 46 | 0.4 | 1.1 |
| 47 | 0.5 | 3.5 |
| 48 | 0.5 | 1.6 |
| 49 | 0.8 | 3.1 |
| 50 | 1.6 | 9.3 |
| 51 | 10.7 | 29.8 |
| 52 | 10 | 33 |
| 53 | 4.3 | 12.4 |
| 54 | 1.6 | 5.9 |
| 55 | 7.5 | 14.8 |
| 57 | 1.7 | 5.1 |
| 58 | 1.4 | 3.9 |
| 59 | 1.6 | 3.8 |
| 60 | 3 | 8.1 |
| 61 | 1.2 | 6.7 |
| 62 | 0.7 | 3.2 |
| 63 | 3.2 | 17.8 |
| 64 | 3.5 | 43 |
| 65 | 2.8 | 14 |
| 66 | 24.6 | 113 |
| 67 | <3.1 | 17.5 |
| 68 | 0.7 | 8 |
| 69 | <3.1 | 17 |
| 70 | <3.1 | 16 |
| 71 | 18 | 62 |
| 72 | 10 | 91 |
| 73 | 3.3 | 26 |
| Chloroquine | 4.2 | 3.8 |
| Artesunate | 2.7 | 1 |

In Vivo Antimalarial Efficacy Studies

In vivo antimalarial activity is assessed for groups of three female NMRI mice (20-22 g) intravenously infected on day 0 with *P. berghei* strain GFP-ANKA (0.2 mL heparinized saline suspension containing $2 \times 10^7$ parasitized erythrocytes). In control mice, parasitemia typically rises to approximately 40% by day 3 after infection. Compounds are formulated in Tween 80/ethanol (7%/3%) usually at concentrations of 10 mg/mL. Compounds are administered in a volume of 10 mL/kg orally as single doses (1×100 mg/kg, 24 h after infection). 48 h after drug treatment (day 3 post-infection), 1 µl tail blood is taken, resuspended in 1 mL PBS buffer and parasitemia determined with a FACScan (Becton Dickinson) by counting 100'000 red blood cells. Activity is calculated as the difference between the mean value of the control group and treated groups expressed as a percent relative to the control group.

TABLE 2

Activity (inhibition of parasitemia) of compounds of formula I after single oral dose of 100 mg/kg expressed as a percent relative to the control group

| Compound of Example # | Activity [%] |
|---|---|
| 1* | <40 |
| 2 | 94.1 |
| 3 | 98.7 |
| 4 | 97.4 |
| 5 | <40 |
| 6 | 80.4 |
| 7 | 44.7 |
| 8 | 99.4 |
| 9 | 99.1 |
| 10 | 96 |
| 15 | 99 |
| 16 | 85.9 |
| 18 | 99.1 |
| 19 | 99.2 |
| 20 | 98.5 |
| 21 | 98.8 |
| 22 | 99.3 |
| 23 | 99.1 |
| 24 | 79.2 |
| 25 | 99.1 |
| 27 | <40 |
| 28 | 99.3 |
| 29 | 99.2 |
| 30 | 97.7 |
| 31 | 88.9 |
| 32 | 98.5 |
| 33 | 97.4 |
| 34 | 99.2 |
| 35 | 98.7 |
| 36 | 46.8 |
| 38 | 98.5 |
| 39 | 99 |
| 40 | 93.6 |
| 41 | 71 |
| 42 | 97.3 |
| 43 | 98.7 |
| 44 | 99.0 |
| 45 | 99.4 |

TABLE 2-continued

Activity (inhibition of parasitemia) of compounds of formula I after single oral dose of 100 mg/kg expressed as a percent relative to the control group

| Compound of Example # | Activity [%] |
|---|---|
| 46 | 98.9 |
| 47 | 98.4 |
| 48 | 99 |
| 49 | 98.6 |
| 50 | 98 |
| 52 | <40 |
| 53 | 52.3 |
| 54 | 93.7 |
| 55 | <40 |
| 57 | 98.2 |
| 58 | 98.2 |
| 59 | 96.5 |
| 60 | 78.3 |
| 61 | 98.8 |
| 62 | 99.4 |

*Reference Example

The invention claimed is:

1. A compound of the formula I:

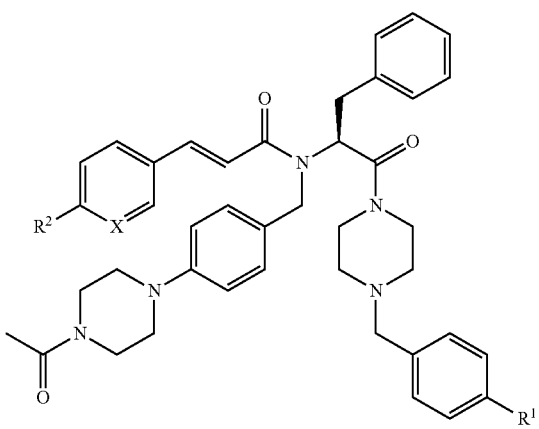

Formula I wherein
X is CH or N;
R$^1$ represents —NO$_2$, —N(CH$_3$)$_2$, or —NCH$_3$(CH$_2$CH$_2$OH); and
R$^2$ represents hydrogen, methyl, ethyl, n-propyl, isopropyl, tert-butyl, cyano, halogen, methoxy, ethoxy, n-propoxy, isopropoxy, trifluoromethyl, difluoromethoxy, methylsulfonyl, acetyl, or acetylamino; or
X is CH, R$^1$ is hydrogen, and R$^2$ is ethyl, isopropyl, tert-butyl, ethoxy, n-propoxy, isopropoxy, methylsulfonyl, acetylamino, or methoxycarbonyl; or
X is CH, R$^1$ is cyano, and R$^2$ is ethyl, isopropyl, tert-butyl, ethoxy, n-propoxy, isopropoxy, trifluoromethyl, difluoromethoxy, trifluoromethoxy, methylsulfonyl, or acetylamino; or
X is CH, R$^1$ is chloro, and R$^2$ is ethyl, isopropyl, tert-butyl, ethoxy, n-propoxy, isopropoxy, difluoromethoxy, methylsulfonyl, or acetylamino; or
X is CH, R$^1$ is methoxy or isopropoxy, and R$^2$ is trifluoromethyl; or
X is CH, R$^1$ is methylsulfonyl or ethylsulfonyl, and R$^2$ is trifluoromethyl, ethyl, isopropyl, tert-butyl, ethoxy, n-propoxy, isopropoxy, or difluoromethoxy;
or a salt of such a compound.

2. The compound according to claim 1, wherein
X is CH or N;
R$^1$ represents —NO$_2$, —N(CH$_3$)$_2$, or —NCH$_3$(CH$_2$CH$_2$OH); and
R$^2$ represents hydrogen, methyl, ethyl, n-propyl, isopropyl, tert-butyl, cyano, halogen, methoxy, ethoxy, n-propoxy, isopropoxy, trifluoromethyl, difluoromethoxy, methylsulfonyl, acetyl, or acetylamino; or
X is CH, R$^1$ is hydrogen, and R$^2$ is ethyl, isopropyl, tert-butyl, ethoxy, n-propoxy, isopropoxy, methylsulfonyl, acetylamino, or methoxycarbonyl; or
X is CH, R$^1$ is cyano, and R$^2$ is ethyl, isopropyl, tert-butyl, ethoxy, n-propoxy, isopropoxy, trifluoromethyl, difluoromethoxy, trifluoromethoxy, methylsulfonyl, or acetylamino; or
X is CH, R$^1$ is chloro, and R$^2$ is ethyl, isopropyl, tert-butyl, ethoxy, n-propoxy, isopropoxy, difluoromethoxy, methylsulfonyl, or acetylamino; or
X is CH, R$^1$ is methoxy or isopropoxy, and R$^2$ is trifluoromethyl;
or a salt of such a compound.

3. The compound according to claim 1, wherein
X is CH or N;
R$^1$ represents —NO$_2$, —N(CH$_3$)$_2$, or —NCH$_3$(CH$_2$CH$_2$OH); and
R$^2$ represents ethyl, isopropyl, tert-butyl, methoxy, ethoxy, n-propoxy, isopropoxy, trifluoromethyl, difluoromethoxy, methylsulfonyl, or acetylamino; or
X is CH, R$^1$ is hydrogen, and R$^2$ is ethyl, isopropyl, tert-butyl, ethoxy, n-propoxy, isopropoxy, methylsulfonyl, acetylamino, or methoxycarbonyl; or
X is CH, R$^1$ is cyano, and R$^2$ is ethyl, isopropyl, tert-butyl, ethoxy, n-propoxy, isopropoxy, trifluoromethyl, difluoromethoxy, trifluoromethoxy, methylsulfonyl, or acetylamino; or
X is CH, R$^1$ is chloro, and R$^2$ is ethyl, isopropyl, tert-butyl, ethoxy, n-propoxy, isopropoxy, difluoromethoxy, methylsulfonyl, or acetylamino; or
X is CH, R$^1$ is methoxy or isopropoxy, and R$^2$ is trifluoromethyl;
or a salt of such a compound.

4. The compound according to claim 1, wherein
R$^1$ represents —NO$_2$, —N(CH$_3$)$_2$, or —NCH$_3$(CH$_2$CH$_2$OH); and
R$^2$ represents hydrogen, methyl, ethyl, n-propyl, isopropyl, tert-butyl, cyano, halogen, methoxy, ethoxy, n-propoxy, isopropoxy, trifluoromethyl, difluoromethoxy, methylsulfonyl, acetyl, or acetylamino;
or a salt of such a compound.

5. The compound according to claim 1, wherein
R$^1$ represents —NO$_2$, —N(CH$_3$)$_2$, or —NCH$_3$(CH$_2$CH$_2$OH); and
R$^2$ represents ethyl, isopropyl, tert-butyl, methoxy, ethoxy, n-propoxy, isopropoxy, trifluoromethyl, difluoromethoxy, methylsulfonyl, or acetylamino;
or a salt of such a compound.

6. The compound according to claim 4, wherein X is CH, or a salt of such a compound.

7. The compound according to claim 4, wherein X is N, or a salt of such a compound.

8. The A compound according to claim 4, wherein R$^1$ represents —NO$_2$, or a salt of such a compound.

9. The compound according to claim 4, wherein $R^1$ represents —N(CH$_3$)$_2$, or a salt of such a compound.

10. The compound according to claim 4, wherein $R^1$ represents —NCH$_3$(CH$_2$CH$_2$OH), or a salt of such a compound.

11. The compound according to claim 4, wherein $R^2$ is ethyl, isopropyl, tert-butyl, ethoxy, n-propoxy, or isopropoxy, or a salt of such a compound.

12. The compound according to claim 11, wherein $R^2$ is isopropoxy, or a salt of such a compound.

13. The compound according to claim 4, wherein $R^2$ is trifluoromethyl, difluoromethoxy, methylsulfonyl, or acetylamino, or a salt of such a compound.

14. The compound according to claim 4, wherein $R^2$ is methoxy, or a salt of such a compound.

15. The compound according to claim 4, wherein $R^2$ is hydrogen, methyl, n-propyl, cyano, halogen, or acetyl, or a salt of such a compound.

16. The compound according to claim 1, selected from the group consisting of:
- (S)—N-[4-(4-Acetyl-piperazin-1-yl)-benzyl]-N-{1-benzyl-2-[4-(4-dimethylamino-benzyl)-piperazin-1-yl]-2-oxo-ethyl}-3-(4-trifluoromethyl-phenyl)-acrylamide,
- (S)—N-[4-(4-Acetyl-piperazin-1-yl)-benzyl]-N-{1-benzyl-2-[4-(4-dimethylamino-benzyl)-piperazin-1-yl]-2-oxo-ethyl}-3-(6-trifluoromethyl-pyridin-3-yl)-acrylamide,
- (S)—N-[4-(4-Acetyl-piperazin-1-yl)-benzyl]-N-{1-benzyl-2-[4-(4-dimethylamino-benzyl)-piperazin-1-yl]-2-oxo-ethyl}-3-(6-methoxy-pyridin-3-yl)-acrylamide,
- (S)—N-[4-(4-Acetyl-piperazin-1-yl)-benzyl]-N-{1-benzyl-2-[4-(4-dimethylamino-benzyl)-piperazin-1-yl]-2-oxo-ethyl}-3-(6-ethoxy-pyridin-3-yl)-acrylamide,
- (S)—N-[4-(4-Acetyl-piperazin-1-yl)-benzyl]-N-{1-benzyl-2-[4-(4-dimethylamino-benzyl)-piperazin-1-yl]-2-oxo-ethyl}-3-(4-ethoxy-phenyl)-acrylamide,
- (S)—N-[4-(4-Acetyl-piperazin-1-yl)-benzyl]-N-{1-benzyl-2-[4-(4-dimethylamino-benzyl)-piperazin-1-yl]-2-oxo-ethyl}-3-(4-methanesulfonyl-phenyl)-acrylamide,
- (S)-3-(4-Acetylamino-phenyl)-N-[4-(4-acetyl-piperazin-1-yl)-benzyl]-N-{1-benzyl-2-[4-(4-dimethylamino-benzyl)-piperazin-1-yl]-2-oxo-ethyl}-acrylamide,
- (S)—N-[4-(4-Acetyl-piperazin-1-yl)-benzyl]-N-{1-benzyl-2-[4-(4-dimethylamino-benzyl)-piperazin-1-yl]-2-oxo-ethyl}-3-(4-propoxy-phenyl)-acrylamide,
- (S)—N-[4-(4-Acetyl-piperazin-1-yl)-benzyl]-N-{1-benzyl-2-[4-(4-dimethylamino-benzyl)-piperazin-1-yl]-2-oxo-ethyl}-3-(4-isopropoxy-phenyl)-acrylamide,
- (S)—N-[4-(4-Acetyl-piperazin-1-yl)-benzyl]-N-{1-benzyl-2-[4-(4-dimethylamino-benzyl)-piperazin-1-yl]-2-oxo-ethyl}-3-(4-ethyl-phenyl)-acrylamide,
- (S)—N-[4-(4-Acetyl-piperazin-1-yl)-benzyl]-N-{1-benzyl-2-[4-(4-dimethylamino-benzyl)-piperazin-1-yl]-2-oxo-ethyl}-3-(4-difluoromethoxy-phenyl)-acrylamide,
- (S)—N-[4-(4-Acetyl-piperazin-1-yl)-benzyl]-N-{1-benzyl-2-[4-(4-dimethylamino-benzyl)-piperazin-1-yl]-2-oxo-ethyl}-3-(4-tert-butyl-phenyl)-acrylamide,
- (S)—N-[4-(4-Acetyl-piperazin-1-yl)-benzyl]-N-{1-benzyl-2-[4-(4-dimethylamino-benzyl)-piperazin-1-yl]-2-oxo-ethyl}-3-(4-isopropyl-phenyl)-acrylamide,
- (S)—N-[4-(4-Acetyl-piperazin-1-yl)-benzyl]-N-[1-benzyl-2-(4-{4-[(2-hydroxy-ethyl)-methyl-amino]-benzyl}-piperazin-1-yl)-2-oxo-ethyl]-3-(4-trifluoromethyl-phenyl)-acrylamide,
- (S)—N-[4-(4-Acetyl-piperazin-1-yl)-benzyl]-N-[1-benzyl-2-(4-{4-[(2-hydroxy-ethyl)-methyl-amino]-benzyl}-piperazin-1-yl)-2-oxo-ethyl]-3-(6-trifluoromethyl-pyridin-3-yl)-acrylamide,
- (S)—N-[4-(4-Acetyl-piperazin-1-yl)-benzyl]-N-[1-benzyl-2-(4-{4-[(2-hydroxy-ethyl)-methyl-amino]-benzyl}-piperazin-1-yl)-2-oxo-ethyl]-3-(6-methoxy-pyridin-3-yl)-acrylamide,
- (S)—N-[4-(4-Acetyl-piperazin-1-yl)-benzyl]-N-[1-benzyl-2-(4-{4-[(2-hydroxy-ethyl)-methyl-amino]-benzyl}-piperazin-1-yl)-2-oxo-ethyl]-3-(6-ethoxy-pyridin-3-yl)-acrylamide,
- (S)—N-[4-(4-Acetyl-piperazin-1-yl)-benzyl]-N-[1-benzyl-2-(4-{4-[(2-hydroxy-ethyl)-methyl-amino]-benzyl}-piperazin-1-yl)-2-oxo-ethyl]-3-(4-ethoxy-phenyl)-acrylamide,
- (S)—N-[4-(4-Acetyl-piperazin-1-yl)-benzyl]-N-[1-benzyl-2-(4-{4-[(2-hydroxy-ethyl)-methyl-amino]-benzyl}-piperazin-1-yl)-2-oxo-ethyl]-3-(4-methanesulfonyl-phenyl)-acrylamide,
- (S)-3-(4-Acetylamino-phenyl)-N-[4-(4-acetyl-piperazin-1-yl)-benzyl]-N-[1-benzyl-2-(4-{4-[(2-hydroxy-ethyl)-methyl-amino]-benzyl}-piperazin-1-yl)-2-oxo-ethyl]-acrylamide,
- (S)—N-[4-(4-Acetyl-piperazin-1-yl)-benzyl]-N-[1-benzyl-2-(4-{4-[(2-hydroxy-ethyl)-methyl-amino]-benzyl}-piperazin-1-yl)-2-oxo-ethyl]-3-(4-propoxy-phenyl)-acrylamide,
- (S)—N-[4-(4-Acetyl-piperazin-1-yl)-benzyl]-N-[1-benzyl-2-(4-{4-[(2-hydroxy-ethyl)-methyl-amino]-benzyl}-piperazin-1-yl)-2-oxo-ethyl]-3-(4-isopropoxy-phenyl)-acrylamide,
- (S)—N-[4-(4-Acetyl-piperazin-1-yl)-benzyl]-N-[1-benzyl-2-(4-{4-[(2-hydroxy-ethyl)-methyl-amino]-benzyl}-piperazin-1-yl)-2-oxo-ethyl]-3-(4-ethyl-phenyl)-acrylamide,
- (S)—N-[4-(4-Acetyl-piperazin-1-yl)-benzyl]-N-[1-benzyl-2-(4-{4-[(2-hydroxy-ethyl)-methyl-amino]-benzyl}-piperazin-1-yl)-2-oxo-ethyl]-3-(4-difluoromethoxy-phenyl)-acrylamide,
- (S)—N-[4-(4-Acetyl-piperazin-1-yl)-benzyl]-N-[1-benzyl-2-(4-{4-[(2-hydroxy-ethyl)-methyl-amino]-benzyl}-piperazin-1-yl)-2-oxo-ethyl]-3-(4-isopropyl-phenyl)-acrylamide,
- (S)—N-[4-(4-Acetyl-piperazin-1-yl)-benzyl]-N-[1-benzyl-2-(4-{4-[(2-hydroxy-ethyl)-methyl-amino]-benzyl}-piperazin-1-yl)-2-oxo-ethyl]-3-(4-tert-butyl-phenyl)-acrylamide, and
- (S)—N-[4-(4-Acetyl-piperazin-1-yl)-benzyl]-N-{1-benzyl-2-[4-(4-nitro-benzyl)-piperazin-1-yl]-2-oxo-ethyl}-3-(4-trifluoromethyl-phenyl)-acrylamide, or salts of these compounds.

17. The compound according to claim 1, selected from the group consisting of:
- (S)—N-[4-(4-Acetyl-piperazin-1-yl)benzyl]-N-{1-(4-(4-(dimethylamino)benzyl)piperazin-1-yl)-1-oxo-3-phenylpropan-2-yl}cinnamamide,
- (S)—N-[4-(4-Acetyl-piperazin-1-yl)benzyl]-N-{1-[4-(4-(dimethylamino)benzyl)piperazin-1-yl]-1-oxo-3-phenylpropan-2-yl}-3-(p-tolyl)acrylamide,
- (S)—N-[4-(4-Acetyl-piperazin-1-yl)benzyl]-N-{1-(4-(4-(dimethylamino)benzyl)piperazin-1-yl)-1-oxo-3-phenylpropan-2-yl}-3-(4-propylphenyl)acrylamide,
- (S)—N-[4-(4-Acetyl-piperazin-1-yl)benzyl]-N-{1-(4-(4-(dimethylamino)benzyl)piperazin-1-yl)-1-oxo-3-phenylpropan-2-yl}-3-(4-methoxyphenyl)acrylamide,
- (S)-3-(4-Acetyl-phenyl)-N-[4-(4-acetyl-piperazin-1-yl)benzyl]-N-{1-(4-(4-(dimethylamino)benzyl)piperazin-1-yl)-1-oxo-3-phenylpropan-2-yl}acrylamide, (S)—N-[4-(4-Acetyl-piperazin-1-yl)benzyl]-3-(4-cyanophenyl)-N-{1-(4-(4-(dimethylamino)benzyl)piperazin-1-yl)-1-oxo-3-phenylpropan-2-yl}acrylamide, (S)—N-[4-(4-Acetyl-piperazin-1-yl)benzyl]-N-{1-(4-(4-(dimethylamino)benzyl)piperazin-1-yl)-1-oxo-3-phenylpropan-2-yl}-3-(4-fluorophenyl)acrylamide, and (S)—N-[4-(4-Acetyl-piperazin-1-yl)benzyl]-3-(4-chlorophenyl)-N-{1-(4-(4-(dimethylamino)benzyl)piperazin-1-yl)-1-oxo-3-phenylpropan-2-yl}acrylamide, or salts of these compounds.

18. The compound according to claim 1, selected from the group consisting of:

(S)—N-[4-(4-Acetyl-piperazin-1-yl)-benzyl]-N-[1-benzyl-2-(4-benzyl-piperazin-1-yl)-2-oxo-ethyl]-3-(4-ethyl-phenyl)-acrylamide, (S)—N-[4-(4-Acetyl-piperazin-1-yl)-benzyl]-N-[1-benzyl-2-(4-benzyl-piperazin-1-yl)-2-oxo-ethyl]-3-(4-tert-butyl-phenyl)-acrylamide, (S)—N-[4-(4-Acetyl-piperazin-1-yl)-benzyl]-N-[1-benzyl-2-(4-benzyl-piperazin-1-yl)-2-oxo-ethyl]-3-(4-ethoxy-phenyl)-acrylamide, (S)-4-(2-{[4-(4-Acetyl-piperazin-1-yl)-benzyl]-[1-benzyl-2-(4-benzyl-piperazin-1-yl)-2-oxo-ethyl]-carbamoyl}-vinyl)-benzoic acid methyl ester, (S)—N-[4-(4-Acetyl-piperazin-1-yl)-benzyl]-N-[1-benzyl-2-(4-benzyl-piperazin-1-yl)-2-oxo-ethyl]-3-(4-methanesulfonyl-phenyl)-acrylamide, (S)-3-(4-Acetylamino-phenyl)-N-[4-(4-acetyl-piperazin-1-yl)-benzyl]-N-[1-benzyl-2-(4-benzyl-piperazin-1-yl)-2-oxo-ethyl]-acrylamide, (S)—N-[4-(4-Acetyl-piperazin-1-yl)-benzyl]-N-[1-benzyl-2-(4-benzyl-piperazin-1-yl)-2-oxo-ethyl]-3-(4-propoxy-phenyl)-acrylamide, (S)—N-[4-(4-Acetyl-piperazin-1-yl)-benzyl]-N-[1-benzyl-2-(4-benzyl-piperazin-1-yl)-2-oxo-ethyl]-3-(4-isopropoxy-phenyl)-acrylamide, (S)—N-[4-(4-Acetyl-piperazin-1-yl)-benzyl]-N-[1-benzyl-2-(4-benzyl-piperazin-1-yl)-2-oxo-ethyl]-3-(4-isopropyl-phenyl)-acrylamide, (S)—N-[4-(4-Acetyl-piperazin-1-yl)-benzyl]-N-{1-benzyl-2-[4-(4-cyano-benzyl)-piperazin-1-yl]-2-oxo-ethyl}-3-(4-trifluoromethyl-phenyl)-acrylamide, (S)—N-[4-(4-Acetyl-piperazin-1-yl)-benzyl]-N-{1-benzyl-2-[4-(4-cyano-benzyl)-piperazin-1-yl]-2-oxo-ethyl}-3-(4-ethoxy-phenyl)-acrylamide, (S)—N-[4-(4-Acetyl-piperazin-1-yl)-benzyl]-N-{1-benzyl-2-[4-(4-cyano-benzyl)-piperazin-1-yl]-2-oxo-ethyl}-3-(4-methanesulfonyl-phenyl)-acrylamide, (S)-3-(4-Acetylamino-phenyl)-N-[4-(4-acetyl-piperazin-1-yl)-benzyl]-N-{1-benzyl-2-[4-(4-cyano-benzyl)-piperazin-1-yl]-2-oxo-ethyl}-acrylamide, (S)—N-[4-(4-Acetyl-piperazin-1-yl)-benzyl]-N-{1-benzyl-2-[4-(4-cyano-benzyl)-piperazin-1-yl]-2-oxo-ethyl}-3-(4-propoxy-phenyl)-acrylamide, (S)—N-[4-(4-Acetyl-piperazin-1-yl)-benzyl]-N-{1-benzyl-2-[4-(4-cyano-benzyl)-piperazin-1-yl]-2-oxo-ethyl}-3-(4-isopropoxy-phenyl)-acrylamide, (S)—N-[4-(4-Acetyl-piperazin-1-yl)-benzyl]-N-{1-benzyl-2-[4-(4-cyano-benzyl)-piperazin-1-yl]-2-oxo-ethyl}-3-(4-ethyl-phenyl)-acrylamide, (S)—N-[4-(4-Acetyl-piperazin-1-yl)-benzyl]-N-{1-benzyl-2-[4-(4-cyano-benzyl)-piperazin-1-yl]-2-oxo-ethyl}-3-(4-difluoromethoxy-phenyl)-acrylamide, (S)—N-[4-(4-Acetyl-piperazin-1-yl)-benzyl]-N-{1-benzyl-2-[4-(4-cyano-benzyl)-piperazin-1-yl]-2-oxo-ethyl}-3-(4-isopropyl-phenyl)-acrylamide, (S)—N-[4-(4-Acetyl-piperazin-1-yl)-benzyl]-N-{1-benzyl-2-[4-(4-cyano-benzyl)-piperazin-1-yl]-2-oxo-ethyl}-3-(4-trifluoromethoxy-phenyl)-acrylamide, (S)—N-[4-(4-Acetyl-piperazin-1-yl)-benzyl]-N-{1-benzyl-2-[4-(4-cyano-benzyl)-piperazin-1-yl]-2-oxo-ethyl}-3-(4-tert-butyl-phenyl)-acrylamide, (S)—N-[4-(4-Acetyl-piperazin-1-yl)-benzyl]-N-{1-benzyl-2-[4-(4-chloro-benzyl)-piperazin-1-yl]-2-oxo-ethyl}-3-(4-ethoxy-phenyl)-acrylamide, (S)—N-[4-(4-Acetyl-piperazin-1-yl)-benzyl]-N-{1-benzyl-2-[4-(4-chloro-benzyl)-piperazin-1-yl]-2-oxo-ethyl}-3-(4-methanesulfonyl-phenyl)-acrylamide, (S)-3-(4-Acetylamino-phenyl)-N-[4-(4-acetyl-piperazin-1-yl)-benzyl]-N-{1-benzyl-2-[4-(4-chloro-benzyl)-piperazin-1-yl]-2-oxo-ethyl}-acrylamide, (S)—N-[4-(4-Acetyl-piperazin-1-yl)-benzyl]-N-{1-benzyl-2-[4-(4-chloro-benzyl)-piperazin-1-yl]-2-oxo-ethyl}-3-(4-propoxy-phenyl)-acrylamide, (S)—N-[4-(4-Acetyl-piperazin-1-yl)-benzyl]-N-{1-benzyl-2-[4-(4-chloro-benzyl)-piperazin-1-yl]-2-oxo-ethyl}-3-(4-isopropoxy-phenyl)-acrylamide, (S)—N-[4-(4-Acetyl-piperazin-1-yl)-benzyl]-N-{1-benzyl-2-[4-(4-chloro-benzyl)-piperazin-1-yl]-2-oxo-ethyl}-3-(4-ethyl-phenyl)-acrylamide, (S)—N-[4-(4-Acetyl-piperazin-1-yl)-benzyl]-N-{1-benzyl-2-[4-(4-chloro-benzyl)-piperazin-1-yl]-2-oxo-ethyl}-3-(4-difluoromethoxy-phenyl)-acrylamide, (S)—N-[4-(4-Acetyl-piperazin-1-yl)-benzyl]-N-{1-benzyl-2-[4-(4-chloro-benzyl)-piperazin-1-yl]-2-oxo-ethyl}-3-(4-isopropyl-phenyl)-acrylamide, (S)—N-[4-(4-Acetyl-piperazin-1-yl)-benzyl]-N-{1-benzyl-2-[4-(4-chloro-benzyl)-piperazin-1-yl]-2-oxo-ethyl}-3-(4-tert-butyl-phenyl)-acrylamide, (S)—N-[4-(4-Acetyl-piperazin-1-yl)-benzyl]-N-{1-benzyl-2-[4-(4-methoxy-benzyl)-piperazin-1-yl]-2-oxo-ethyl}-3-(4-trifluoromethyl-phenyl)-acrylamide, and (S)—N-[4-(4-Acetyl-piperazin-1-yl)-benzyl]-N-{1-benzyl-2-[4-(4-isopropoxy-benzyl)-piperazin-1-yl]-2-oxo-ethyl}-3-(4-trifluoromethyl-phenyl)-acrylamide, or salts of these compounds.

19. The compound according to claim 1, selected from the group consisting of:

(S)—N-[4-(4-Acetyl-piperazin-1-yl)-benzyl]-N-{1-benzyl-2-[4-(4-(methylsulfonyl)-benzyl)-piperazin-1-yl]-2-oxo-ethyl}-3-(4-isopropoxyphenyl)-acrylamide, (S)—N-[4-(4-Acetyl-piperazin-1-yl)-benzyl]-N-{1-benzyl-2-[4-(4-(methylsulfonyl)-benzyl)-piperazin-1-yl]-2-oxo-ethyl}-3-(4-tert-butyl-phenyl)-acrylamide, (S)—N-[4-(4-Acetyl-piperazin-1-yl)-benzyl]-N-{1-benzyl-2-[4-(4-(methylsulfonyl)-benzyl)-piperazin-1-yl]-2-oxo-ethyl}-3-(4-propoxyphenyl)-acrylamide, (S)—N-(4-(4-acetylpiperazin-1-yl)benzyl)-N-(1-(4-(4-(methylsulfonyl)benzyl)piperazin-1-yl)-1-oxo-3-phenylpropan-2-yl)-3-(4-(trifluoromethyl)phenyl)acrylamide, (S)—N-[4-(4-Acetyl-piperazin-1-yl)-benzyl]-N-{1-benzyl-2-[4-(4-(ethylsulfonyl)-benzyl)-piperazin-1-yl]-2-oxo-ethyl}-3-(4-propoxyphenyl)-acrylamide, and (S)—N-(4-(4-acetylpiperazin-1-yl)benzyl)-N-(1-(4-(4-(ethylsulfonyl)benzyl)piperazin-1-yl)-1-oxo-3-phenylpropan-2-yl)-3-(4-(trifluoromethyl)phenyl)acrylamide, or salts of these compounds.

20. A pharmaceutical composition comprising a compound according to claim 1, or a pharmaceutically acceptable salt thereof, and a pharmaceutically acceptable carrier material.

21. A method for the treatment of malaria comprising administering to a subject a pharmaceutically active amount of the compound according to claim 1, or a pharmaceutically acceptable salt thereof.

22. A compound according to claim 1, which is (S)—N-[4-(4-acetyl-piperazin-1-yl)-benzyl]-N-{1-benzyl-2-[4-(4-dimethylamino-benzyl)-piperazin-1-yl]-2-oxo-ethyl}-3-(4-tert-butyl-phenyl)-acrylamide, or a salt thereof.

23. A compound according to claim 1, which is (S)—N-[4-(4-acetyl-piperazin-1-yl)-benzyl]-N-{1-benzyl-2-[4-(4-cyano-benzyl)-piperazin-1-yl]-2-oxo-ethyl}-3-(4-propoxy-phenyl)-acrylamide, or a salt thereof.

24. A compound according to claim 1, which is (S)—N-[4-(4-acetyl-piperazin-1-yl)-benzyl]-N-{1-benzyl-2-[4-(4-cyano-benzyl)-piperazin-1-yl]-2-oxo-ethyl}-3-(4-tert-butyl-phenyl)-acrylamide, or a salt thereof.

25. A compound according to claim 1, which is (S)—N-[4-(4-acetyl-piperazin-1-yl)-benzyl]-N-{1-benzyl-2-[4-(4-(methylsulfonyl)-benzyl)-piperazin-1-yl]-2-oxo-ethyl}-3-(4-tert-butyl-phenyl)-acrylamide, or a salt thereof.

26. A compound according to claim 1, which is (S)—N-[4-(4-acetyl-piperazin-1-yl)-benzyl]-N-[1-benzyl-2-(4-{4-[(2-hydroxy-ethyl)-methyl-amino]-benzyl}-piperazin-1-yl)-2-oxo-ethyl]-3-(4-tert-butyl-phenyl)-acrylamide, or a salt thereof.

27. The pharmaceutical composition according to claim 20, wherein the compound is (S)—N-[4-(4-acetyl-piperazin-1-yl)-benzyl]-N-{1-benzyl-2-[4-(4-dimethylamino-benzyl)-piperazin-1-yl]-2-oxo-ethyl}-3-(4-tert-butyl-phenyl)-acrylamide, or a pharmaceutically acceptable salt thereof.

28. The pharmaceutical composition according to claim 20, wherein the compound is (S)—N-[4-(4-acetyl-piperazin-1-yl)-benzyl]-N-{1-benzyl-2-[4-(4-cyano-benzyl)-piperazin-1-yl]-2-oxo-ethyl}-3-(4-propoxy-phenyl)-acrylamide, or a pharmaceutically acceptable salt thereof.

29. The pharmaceutical composition according to claim 20, wherein the compound is (S)—N-[4-(4-acetyl-piperazin-1-yl)-benzyl]-N-{1-benzyl-2-[4-(4-cyano-benzyl)-piperazin-1-yl]-2-oxo-ethyl}-3-(4-tert-butyl-phenyl)-acrylamide, or a pharmaceutically acceptable salt thereof.

30. The pharmaceutical composition according to claim 20, wherein the compound is (S)—N-[4-(4-acetyl-piperazin-1-yl)-benzyl]-N-{1-benzyl-2-[4-(4-(methylsulfonyl)-benzyl)-piperazin-1-yl]-2-oxo-ethyl}-3-(4-tert-butyl-phenyl)-acrylamide, or a pharmaceutically acceptable salt thereof.

31. The pharmaceutical composition according to claim 20, wherein the compound is (S)—N-[4-(4-acetyl-piperazin-1-yl)-benzyl]-N-[1-benzyl-2-(4-{4-[(2-hydroxy-ethyl)-methyl-amino]-benzyl}-piperazin-1-yl)-2-oxo-ethyl]-3-(4-tert-butyl-phenyl)-acrylamide, or a pharmaceutically acceptable salt thereof.

32. The method according to claim 21, wherein the compound is (S)—N-[4-(4-acetyl-piperazin-1-yl)-benzyl]-N-{1-benzyl-2-[4-(4-dimethylamino-benzyl)-piperazin-1-yl]-2-oxo-ethyl}-3-(4-tert-butyl-phenyl)-acrylamide, or a pharmaceutically acceptable salt thereof.

33. The method according to claim 21, wherein the compound is (S)—N-[4-(4-acetyl-piperazin-1-yl)-benzyl]-N-{1-benzyl-2-[4-(4-cyano-benzyl)-piperazin-1-yl]-2-oxo-ethyl}-3-(4-propoxy-phenyl)-acrylamide, or a pharmaceutically acceptable salt thereof.

34. The method according to claim 21, wherein the compound is (S)—N-[4-(4-acetyl-piperazin-1-yl)-benzyl]-N-{1-benzyl-2-[4-(4-cyano-benzyl)-piperazin-1-yl]-2-oxo-ethyl}-3-(4-tert-butyl-phenyl)-acrylamide, or a pharmaceutically acceptable salt thereof.

35. The method according to claim 21, wherein the compound is (S)—N-[4-(4-acetyl-piperazin-1-yl)-benzyl]-N-{1-benzyl-2-[4-(4-(methylsulfonyl)-benzyl)-piperazin-1-yl]-2-oxo-ethyl}-3-(4-tert-butyl-phenyl)-acrylamide, or a pharmaceutically acceptable salt thereof.

36. The method according to claim 21, wherein the compound is (S)—N-[4-(4-acetyl-piperazin-1-yl)-benzyl]-N-[1-benzyl-2-(4-{4-[(2-hydroxy-ethyl)-methyl-amino]-benzyl}-piperazin-1-yl)-2-oxo-ethyl]-3-(4-tert-butyl-phenyl)-acrylamide, or a pharmaceutically acceptable salt thereof.

\* \* \* \* \*